(12) United States Patent
Battiste

(10) Patent No.: US 7,433,761 B2
(45) Date of Patent: Oct. 7, 2008

(54) METHOD AND APPARATUS FOR MONITORING POLYOLEFIN PRODUCTION

(75) Inventor: David R. Battiste, Bartlesville, OK (US)

(73) Assignee: Chevron Philips Chemical Company, LP, Woodlands, TX (US)

( * ) Notice: Subject to any disclaimer, the term of this patent is extended or adjusted under 35 U.S.C. 154(b) by 240 days.

(21) Appl. No.: 10/950,249

(22) Filed: Sep. 24, 2004

(65) Prior Publication Data

US 2005/0154154 A1 Jul. 14, 2005

Related U.S. Application Data

(63) Continuation of application No. 10/758,454, filed on Jan. 14, 2004.

(51) Int. Cl.
*G01J 3/44* (2006.01)
*C08F 2/00* (2006.01)
*C08F 2/38* (2006.01)

(52) U.S. Cl. ............... 700/269; 526/59; 526/60; 702/30; 356/301; 264/408; 264/409

(58) Field of Classification Search ........... 526/59, 526/60; 702/22, 30; 700/269; 356/301; 264/408, 409
See application file for complete search history.

(56) References Cited

U.S. PATENT DOCUMENTS

| | | | | |
|---|---|---|---|---|
| 4,888,704 A | | 12/1989 | Topliss et al. | 364/500 |
| 5,151,474 A | | 9/1992 | Lange et al. | 526/66 |
| 5,652,653 A | | 7/1997 | Alsmeyer et al. | 356/301 |
| 5,678,751 A | | 10/1997 | Buchanan et al. | 228/124.6 |
| 5,682,309 A | | 10/1997 | Bartusiak et al. | 364/149 |
| 6,045,661 A | * | 4/2000 | Kreischer et al. | 203/73 |
| 6,072,576 A | | 6/2000 | McDonald et al. | 356/300 |
| 6,479,597 B1 | | 11/2002 | Long et al. | 526/59 |
| 2004/0133364 A1 | * | 7/2004 | Marrow et al. | 702/30 |
| 2004/0136882 A1 | * | 7/2004 | Verser et al. | 422/132 |
| 2006/0136149 A1 | * | 6/2006 | Long et al. | 702/22 |

FOREIGN PATENT DOCUMENTS

| WO | WO 96 41822 A | 12/1996 |
|---|---|---|
| WO | WO 01/09203 A1 | 2/2001 |

OTHER PUBLICATIONS

Battiste, David R., et al., On-Line Raman Analysis of Ethylene and Hexene in the Phillips 1-Hexene and Polyethylene Processes, Gulf Coast Conference, Paper Presentation, Abstract #016, Year 2000.

* cited by examiner

*Primary Examiner*—Fred M Teskin
(74) *Attorney, Agent, or Firm*—Fletcher Yoder

(57) ABSTRACT

The present technique provides for the use of spectroscopic probes, such as Raman probes, within the conduits of a polyolefin production system. The Raman probe or other spectroscopic probes may be used to obtain spectroscopic measurements of the contents of the conduits. The spectroscopic measurements may be processed and analyzed to determine the composition of the conduit contents. In addition, the spectroscopic measurements may be used in conjunction with correlations or other statistical models to determine one or more properties of interest of a constituent of the conduit contents. One or more processes upstream and/or downstream of the conduit may be adjusted in response to the determined composition or composition properties.

46 Claims, 28 Drawing Sheets

METHOD AND APPARATUS FOR MONITORING POLYOLEFIN PRODUCTION

CROSS REFERENCE TO RELATED APPLICATIONS

This is a continuation of application U.S. Ser. No. 10/758,454, filed Jan. 14, 2004.

BACKGROUND OF THE INVENTION

1. Field of the Invention

The present invention relates generally to the monitoring and/or control of chemical and petrochemical production and, more specifically, to the use of Raman spectrometry in the monitoring and/or control of polyolefin production.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

As chemical and petrochemical technologies have advanced, the products of these technologies have become increasingly prevalent in society. In particular, as techniques for bonding simple molecular building blocks into longer chains, or polymers, have advanced, the polymer products, typically in the form of various plastics, have been increasingly incorporated into various everyday items. For example, polyolefin polymers, such as polyethylene and polypropylene and their copolymers, are used for retail and pharmaceutical packaging, food and beverage packaging (such as juice and soda bottles), household containers (such as pails and boxes), household items (such as appliances, furniture, carpeting, and toys), automobile components, pipes, conduits, and various industrial products.

Specific types of polyolefins, such as high density polyethylene (HDPE), have particular applications in the manufacture of blow-molded and injection-molded goods, such as food and beverage containers, film, and plastic pipe. Other types of polyolefins, such as low density polyethylene (LDPE), linear low density polyethylene (LLDPE), isotactic polypropylene (iPP), and syndiotactic polypropylene (sPP) are also suited for similar applications. The mechanical requirements of the application, such as tensile strength and density, and/or the chemical requirements, such thermal stability, molecular weight, and chemical reactivity, typically determine what polyolefin or type of polyolefin is suitable.

One benefit of polyolefin construction, as may be deduced from the list of uses above, is that it is generally non-reactive with goods or products with which it is in contact. This allows polyolefin products to be used in residential, commercial, and industrial contexts, including food and beverage storage and transportation, consumer electronics, agriculture, shipping, and vehicular construction. The wide variety of residential, commercial and industrial uses for polyolefins has translated into a substantial demand for raw polyolefin which can be extruded, injected, blown or otherwise formed into a final consumable product or component.

To satisfy this demand, various processes exist by which olefins may be polymerized to form polyolefins. Typically, these processes are performed at petrochemical facilities, which have ready access to the short-chain olefin molecules such as ethylene, propylene, butene, pentene, hexene, octene, and other building blocks of the much longer polyolefin polymers. Regardless of which process is used, the polyolefin product may deviate from the desired product in various ways. For example, the polyolefin product may have a different mechanical properties, such as density, hardness, or flexibility, and/or chemical properties, such as melting temperature or melt flow index, than what is desired. These deviations may arise for various reasons, such as varying catalyst activity, reactant purity, improper reaction conditions, transitions between product grades, and so on. However, if the deviation is not discovered until late in the reaction process, significant resources, both in material and energy, may be spent producing an unacceptable polyolefin product.

Similarly, after the polyolefin product is produced, further downstream processing, such as extrusion and additive addition, may occur. These downstream processes offer further opportunity for deviation from the desired final product and may also result in wasted resources if the deviations are not discovered in a timely manner. Therefore, both in the production and in the processing of the polyolefin product, it is desirable to discover deviations as rapidly as possible and, where appropriate, to make corrections to the processes to minimize the waste of product or resources.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present invention provides a novel technique that aids in the production of polyolefin and other chemical products. In particular, monitoring and/or control of production are enhanced by the use of monitoring equipment, such as Raman spectrographic equipment, which rapidly provides information about the ongoing processes. The monitoring equipment may be strategically positioned in the production process to allow upstream or downstream adjustment of the process based upon the acquired measurements.

In order to facilitate presentation of the present technique, the disclosure is broken into a number of sections. Section I provides an overview of polyolefin production, a discussion of monitoring techniques and technology, particularly Raman spectrometry, and various control methodologies which may be integrated with the monitoring techniques. Section II provides a series of examples of where and how the monitoring and/or control techniques described herein may be employed. In particular, the examples provided, while not exhaustive, encompass a range of possibilities in the polyolefin production process as well as in the subsequent sale and manufacture of the polyolefin. In order to maintain the integrity of these topics and to facilitate description, the reader may, on occasion, be referred to a topic or figures in a different section for a more thorough treatment of an aspect of the techniques.

I. Polyolefin Production Overview

Figure 1:
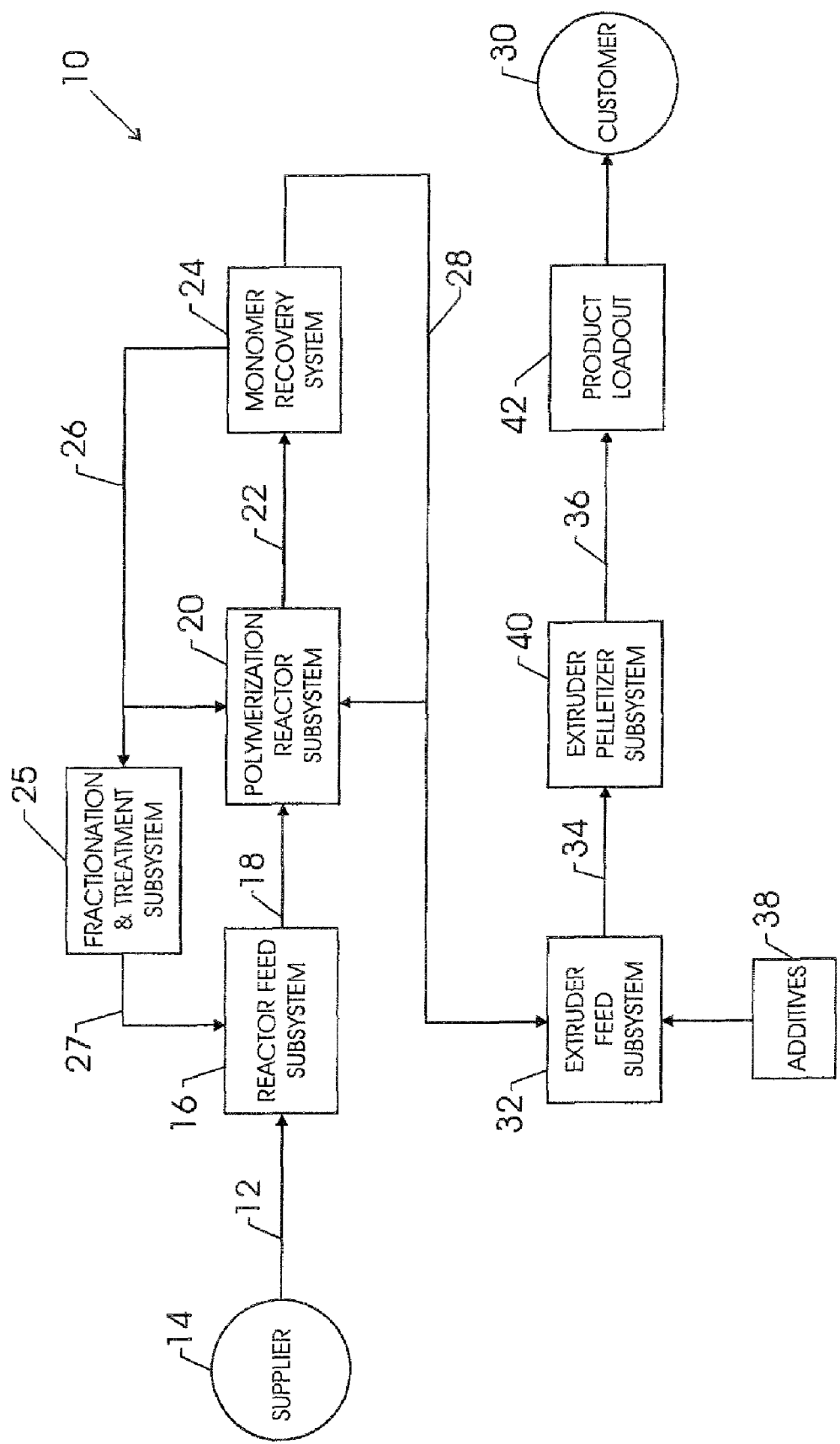
FIG. 1 is a block diagram depicting an exemplary polyolefin manufacturing system for producing polyolefins in accordance with one embodiment of the present techniques.

Turning now to the drawings, and referring initially to FIG. 1, a block diagram depicts an exemplary manufacturing system 10 for producing polyolefins, such as polyethylene, polypropylene and/or their copolymers. One or more reactor feedstocks 12 may be provided to the manufacturing system 10 by a supplier 14 or from local generation and/or storage capabilities at the system 10. The one or more feedstocks 12 may be provided via pipeline, trucks, cylinders, drums, or the like. If more than one feedstock 12 is provided, the feedstocks 12 may be provided separately or jointly, i.e., mixed. Examples of possible feedstocks 12 include various olefin monomers, such as ethylene, propylene, butene, hexene, octene, and so forth.

The reactor feedstock 12 may be provided to a reactor feed subsystem 16 that controls the addition rate of one or more reactor feed streams 18 to a polymerization reactor subsystem 20. The reactor feed streams 18 may be liquid, gaseous, or a supercritical fluid, depending on the type of reactor being fed. The reactor feed streams 18 may include separate and/or mixed streams of olefin monomers and comonomers as well as chain transfer agents, such as hydrogen. The feed streams 18 may also include diluents (such as propane, isobutane, n-hexane, and n-heptane), catalysts (such as Ziegler-Natta catalysts, chromium catalysts, metallocene catalysts, and mixed ZN-metallocene catalysts), co-catalysts (such as triethylaluminum, triethylboron, and methyl aluminoxane), and other additives. The feed subsystem 16 controls the addition rates of the feed streams 18 to the reactor subsystem 20 to maintain the desired reactor stability and/or to achieve the desired polyolefin properties or production rate. In addition, the feed subsystem 16 may prepare or condition one or more catalysts for addition to the reactor subsystem 20.

The reactor subsystem 20 may comprise one or more reactor vessels, such as liquid-phase or gas-phase reactors. The reactor subsystem 20 may also comprise a combination of liquid and gas-phase reactors. If multiple reactors comprise the reactor subsystem 20, the reactors may be arranged in series, in parallel, or in some combination configuration.

Within the reactor subsystem 20, one or more olefin monomers, introduced via the feed streams 18, polymerize to form a product comprising polymer particulates, typically called fluff or granules. The fluff may possess one or more melt, physical, Theological, and/or mechanical properties of interest, such as density, melt index, copolymer comonomer, modulus, crystallinity, melt flow rate, and/or melt index (MFR) and/or copolymer content. The reaction conditions within the reactor subsystem 20, such as temperature, pressure, flow rate, mechanical agitation, product takeoff, and so forth, may be selected to achieve the desired fluff properties.

In addition to the one or more olefin monomers, the one or more feed streams 18 may introduce a diluent into the reactor subsystem 20. The diluent may be an inert hydrocarbon that is liquid at reaction conditions, such as isobutane, propane, n-pentane, i-pentane, neopentane, and n-hexane. Likewise, a catalyst, which is suitable for polymerizing the monomers, may be added to the reactor subsystem 20 via the one or more feed streams 18. For example, in a liquid-phase reactor, the catalyst may be a particle added via a liquid feed stream and suspended in the fluid medium within the reactor. An example of such a catalyst is a chromium oxide containing a hexavalent chromium on a silica support.

A motive device (not shown) may be present within the reactors comprising the reactor subsystem 20. For example, within a liquid-phase reactor, such as a loop-slurry reactor, an impeller may be present and may create a turbulent mixing zone within the fluid medium. The impeller may be driven by a motor or other motive force to propel the fluid medium as well as any catalyst, polyolefin fluff, or other solid particulates suspended within the fluid medium, through the closed loop of the reactor. Similarly, within a gas-phase reactor, such as a fluidized bed reactor, one or more paddles or stirrers may be present and may mix the solid particles within the reactor.

The discharge 22 of the reactor subsystem 20 may include the polymer fluff as well as non-polymer components, such as monomer, comonomer, catalysts, or diluent, from the reactor subsystem 22. The discharge 22 may be subsequently processed, such as by a monomer/diluent recovery subsystem 24, to separate the non-polymer components 26 from the polymer fluff 28. The untreated recovered non-polymer components 26 may be returned to the reactor subsystem 20 or may be treated, such as by a fractionation and treatment subsystem 25, and returned to the feed subsystem 16 as purified components 27. The fluff 28 may also be returned to the reactor subsystem 20 for further polymerization, such as in a different type of reactor or under different reaction conditions, or may be further processed to prepare it for shipment to a customer 30.

The fluff 28 is normally not sent to customers 30 as product. Instead, the fluff 28 is typically sent to an extruder feed subsystem 32 where the fluff 28 may be temporarily stored, such as in silos, to await further processing. Different fluff products 28 may be commingled in the extruder feed subsystem 32 to produce an extruder feed 34 which, when extruded, will produce polymer pellets 36 with the desired mechanical, physical, and melt characteristics. The extruder feed 34 may also comprise additives 38, such as UV inhibitors and peroxides, which are added to the fluff products 28 to impart desired characteristics to the extruded polymer pellets 36.

An extruder/pelletizer 40 receives the extruder feed 34, comprising one or more fluff products 28 and whatever additives 38 have been added. The extruder/pelletizer 40 heats and melts the extruder feed 34. The melted extruder feed 34 may then be extruded through a die under pressure to form polyolefin pellets 36. The polyolefin pellets 36 may then be transported to a product load-out area 42 where the pellets 36 may be stored, blended with other pellets 36, and/or loaded into railcars, trucks, bags, and so forth, for distribution to customers 30.

A. Monitoring

The present techniques are directed to the incorporation of monitoring technologies into the processes described above such that the monitoring data is rapidly available to an operator and/or to automated routines. The monitoring data may be available in real-time or near real-time, i.e., within five minutes. Furthermore, the monitoring data may be obtained from contents within the production process, i.e., on-line, or from samples removed from the production process, i.e., off-line. Raman spectrometry will be discussed herein as one such possible monitoring technology. Though Raman spectrometry and techniques are discussed extensively herein, it is to be understood that the present techniques are applicable to other monitoring technologies capable of real-time or near real-time monitoring and capable of use in on-line processing.

Figure 2:
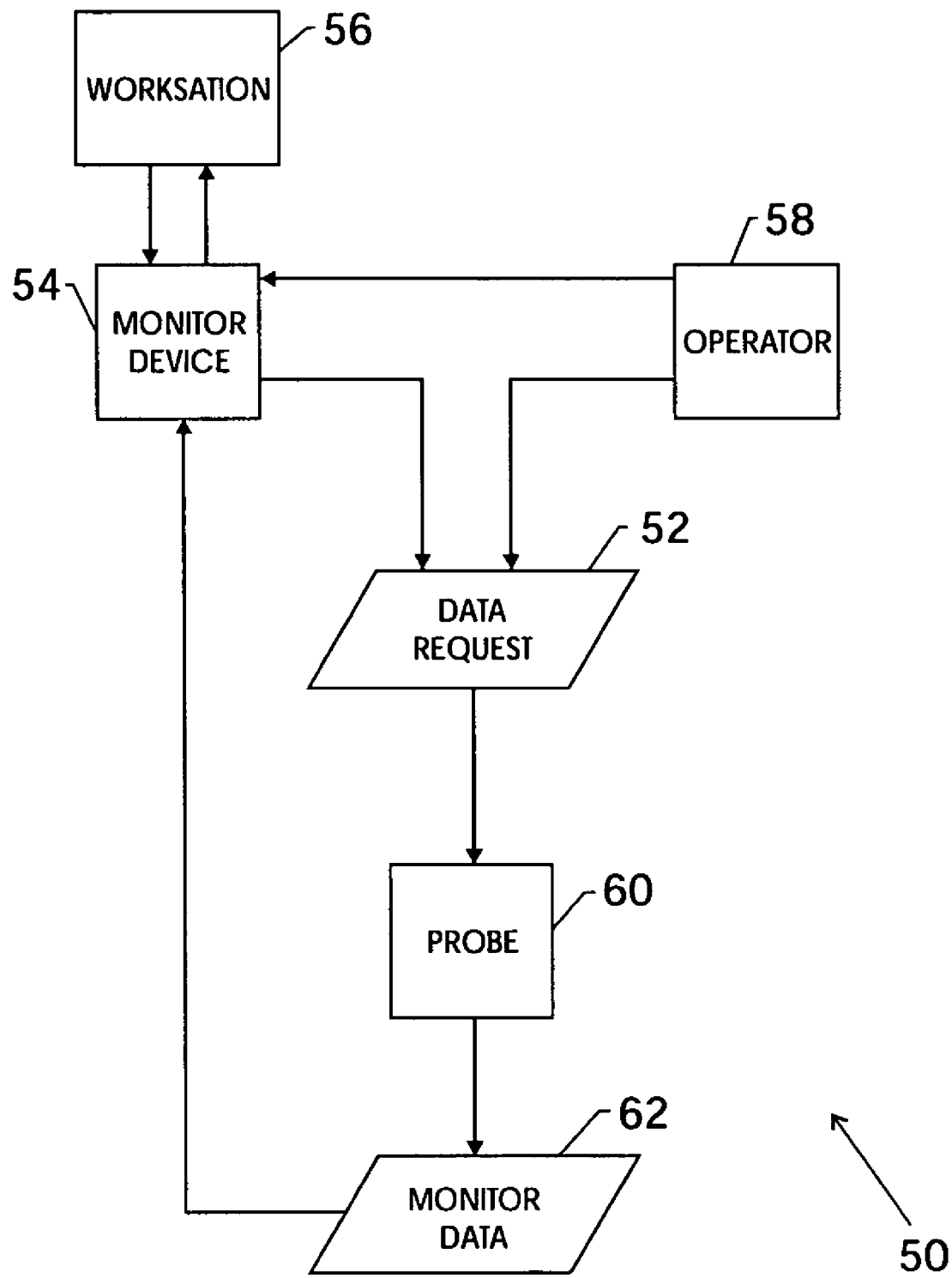
FIG. 2 is a flow chart depicting a monitoring routine in accordance with one embodiment of the present techniques.

For example, referring to FIG. 2, an exemplary monitoring routine 50 is depicted. The monitoring routine 50 may begin with a data request 52, which may be generated automatically by a computer routine executed at a monitor device 54, such as a source/controller used for Raman spectrometry, or at a computer or workstation 56 in communication with the device 54. The data request 52 may also be generated by an operator 58 or by an operator 58 in communication with the monitor device 54. The data request 52 may be transmitted to a probe 60 or other monitoring apparatus configured to obtain the desired monitor data 62, such as a Raman spectrum, from a sample. The probe 60, in response, transmits the acquired monitor data 62, such as the spectra, to the monitor device 54.

The monitor device 54 may provide the data 62 to a computer or operator workstation 56, such as may be found at a distributed control center. The data 62 may then be processed, such as by statistical modeling, at the computer or operator workstation 56 to a more useful form, such as a chemical concentration, a physical, mechanical, or melt property, or even a recommended action. Alternatively, the monitor device 54, such as a Raman source/detector, may process the monitor data 62 before providing it to a computer or operator workstation 56. As used herein, the monitor data 62 should be understood to encompass not only the raw monitor data or spectra acquired by the probe 60, but also processed monitor data, including processed spectra or the results of subjecting raw data to a statistical analysis, such as partial least squares regression or other regression techniques.

Figure 3A:
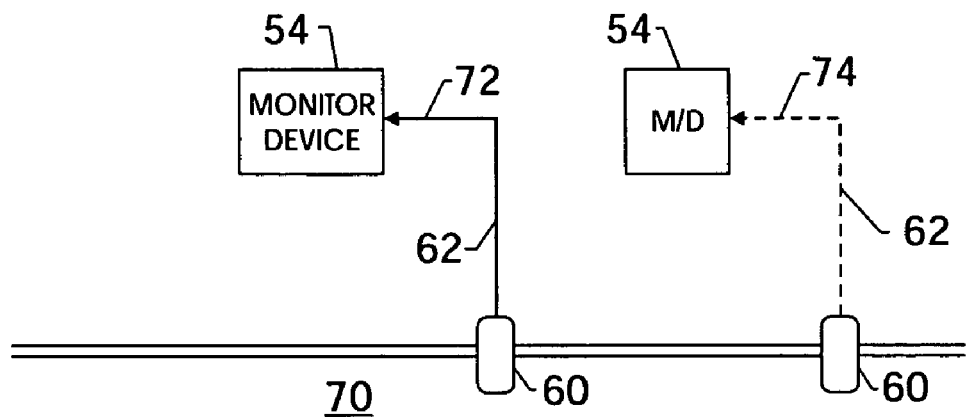
FIG. 3A is a block diagram depicting automatic monitoring of a sample environment in accordance with one embodiment of the present techniques.

Regardless of the monitoring technology employed, it is anticipated that the general monitoring techniques discussed above may be implemented in a variety of ways. For example, referring to FIG. 3A, monitoring may be automatic with a monitor probe 60 situated in the sample environment 70 sending a continuous stream 72 of monitor data 62, such as Raman spectra, to a monitor device 54, such as a source/detector in Raman spectrometry. The monitor device 54 may be configured to receive and/or process the monitor data 62. Alternately the monitor probe 60 may automatically send a discontinuous stream 74 of monitor data 62 to the monitor device 54, such as upon a schedule or upon a conditional basis. For example, the monitor data 62 may be automatically sent when factors such as temperature, pressure, time, or product takeoff exceed configured threshold values.

Figure 3B:
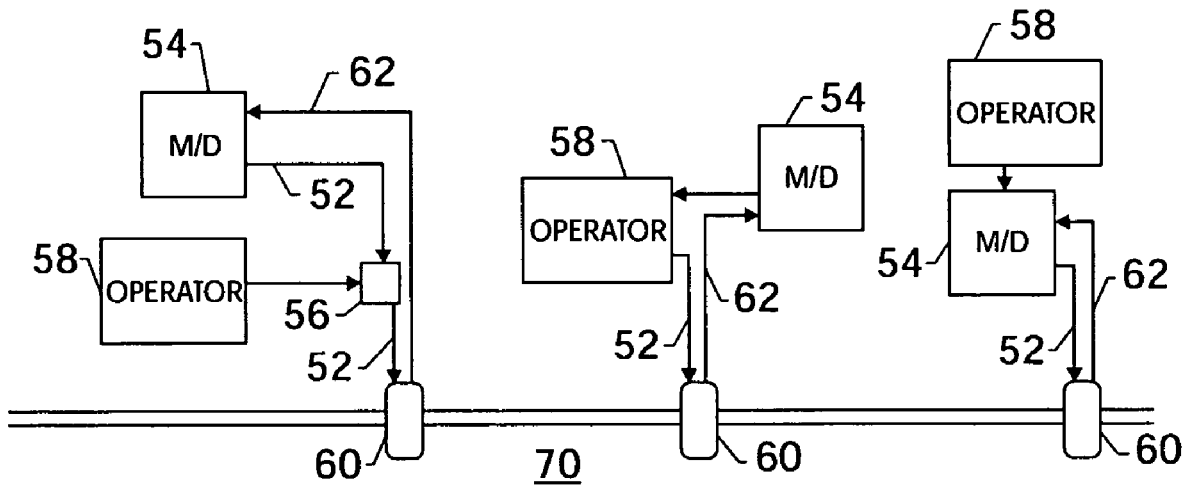
FIG. 3B is a block diagram depicting semi- automatic monitoring of a sample environment in accordance with one embodiment of the present techniques.

Monitoring may also be performed in a partially or semi-automated manner, as depicted in FIG. 3B. In such an implementation, some degree of operator intervention, such as for initiation, execution, and/or sample retrieval, may be involved in the monitoring process. For example, the monitor device 54 may transmit a data request 52 to the probe 60 in the sample environment 70. An operator 58, however, may be required to take some action to complete the transmission to the monitor probe 60, thereby initiating data acquisition and return of the monitor data 62. For example, the operator 58 may be required to acknowledge the request, such as by interacting with the monitor device 54 or an operator workstation 56, before the request 52 is transmitted to the probe 60. Likewise, the operator 58 may be required to provide a sample to be monitored to the probe 60, such as in batch sample or off-line monitoring process, prior to initiating probe activity.

Figure 3C:
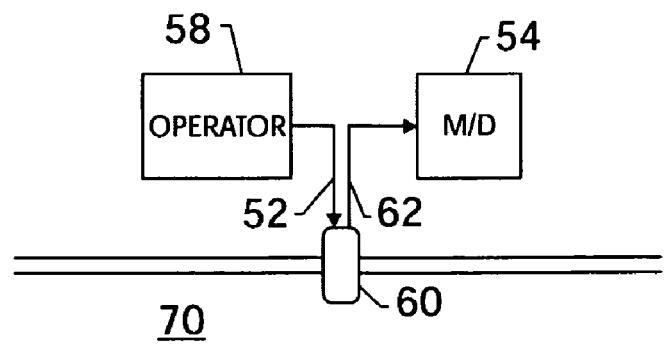
FIG. 3C is a block diagram depicting manual monitoring of a sample environment in accordance with one embodiment of the present techniques.

Alternately, the monitor device 54 may provide the operator 58 with a reminder message or data request 52 to prompt the operator 58 to operate the probe 60. After operation the probe 60 transmits the requested data 62 to the monitor device 54. Furthermore, the operator 58 may instead prompt the monitor device 54 to initiate a data request 52 to the probe 60 with the requested data 62 being transmitted to the device 54. While these various possibilities explain some ways in which the monitoring activity of the monitor device 54 and probe 60 may be partially automated, other combinations of operator action and automated process exist and are to be understood as falling within the scope of partially automated monitoring techniques as used herein. In addition, the monitoring process may be essentially manual, utilizing an operator 58 to initiate the monitoring operation, as depicted in FIG. 3C.

The acquired monitor data 62 is then transmitted to the monitor device 54.

1. Raman Spectrometry a. Overview and Exemplary Systems

As noted above, one suitable technique for on-line and substantially real time monitoring of polyolefin production processes is Raman spectrometry. Raman spectrometry is a form of vibrational spectrometry which utilizes a laser to illuminate a sample and analyzes the reflected or backscattered radiation. The energy shift between the measured reflected radiation and the laser line, i.e., the wavelength of the laser, is equal to the vibrational frequencies of the bonds in the molecules being illuminated. The vibrational frequencies depend on the masses of the atoms in the molecules and on the strength of the interatomic bonds within the molecule, with different bonds, such as C—H or C—C, being characterized by specific frequencies. The vibrational frequency may also depend on the geometric arrangement of atoms in the molecules.

A Raman spectrum generally comprises a plot of the intensity by the energy shift, i.e., Raman shift, of the reflected radiation. In particular, each observation or data point at a wavelength, measured in $cm^{-1}$, comprises a count at that wavelength. The plot of the aggregated counts at each wavelength yields the Raman spectrum for the sample during the measured time period. For pure samples, the spectrum may be used to directly identify the sample. For complex mixtures or solutions, the frequency composition may be broken down by statistical analyses, such as partial least squares analysis, to determine the composition of the sample. In practice, the peak distribution associated with a chemical may serve as a known signature or fingerprint for recognizing that chemical within a mixture or solution. In addition to these quantitative and qualitative advantages, Raman spectrometry has the additional advantages of being spatially resolved, i.e., resolvable at a depth within a sample, and of providing rapid, near-instantaneous response because sample preparation is generally not required.

Figure 4:
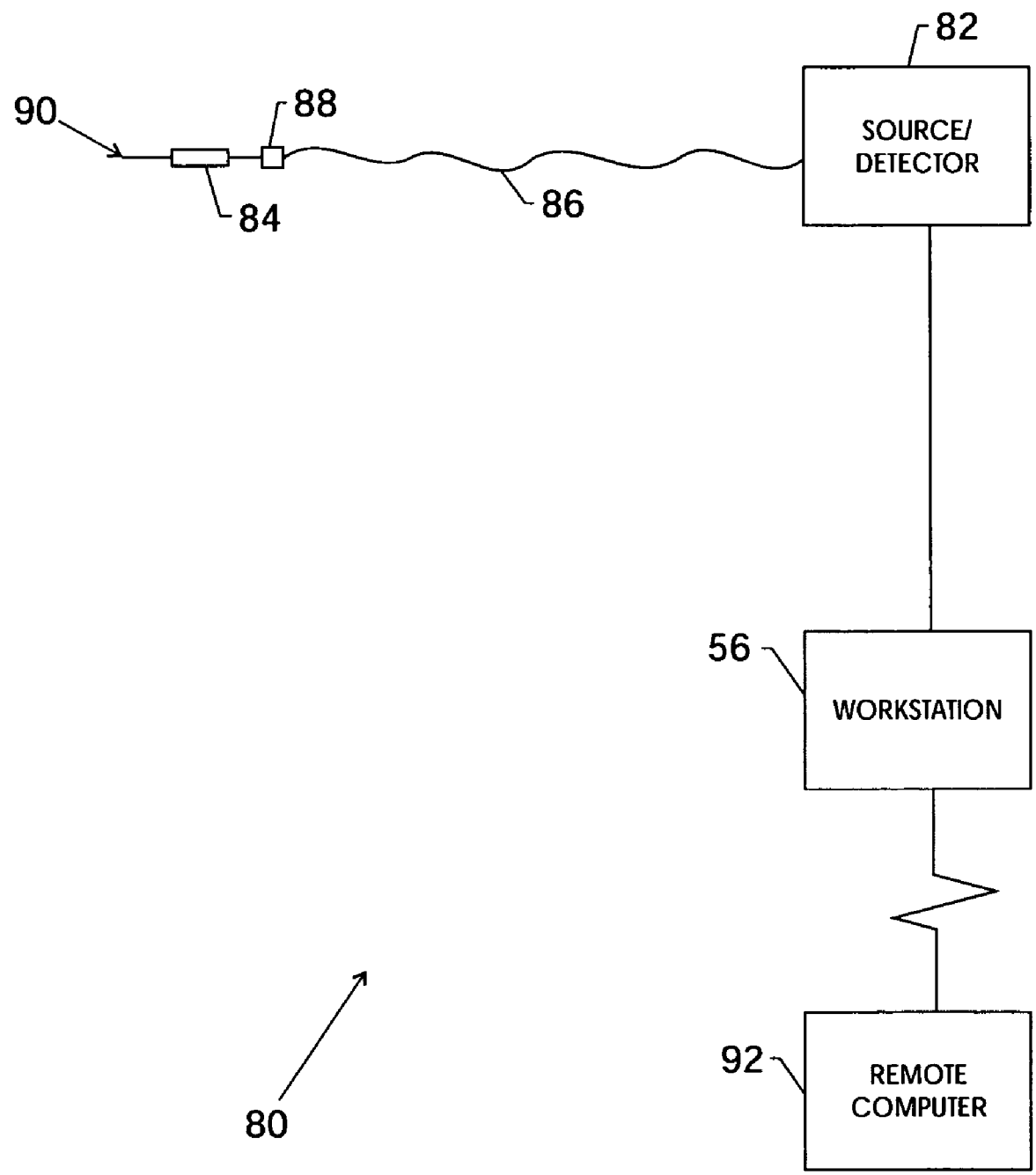
FIG. 4 is a block diagram depicting the components of a Raman spectrographic system in accordance with one embodiment of the present techniques.

An exemplary Raman spectroscopic system 80 is depicted in FIG. 4. As depicted the, spectroscopic system 80 may include a source/detector 82 which generates laser radiation of one or more specified wavelengths. The laser radiation is transmitted to a Raman probe 84 via a fiber optic cable 86. The cable 86 may be connected to the probe 84 via an optical connector/terminator 88 at the end of the probe 84 or may be integrally connected to the probe 84. The cable 86 is typically comprised of two or more fiber optic strands with a portion of the strands, such as the core strands, configured to carry the laser radiation from the source/detector 82 to the probe 84 and the remainder of the strands, i.e., the periphery strands, being configured to carry the reflected radiation to the source/detector 82. The laser radiation passes to and from the sample via a lens 90 at the tip of the probe 84 which is substantially transparent to the incoming and outgoing light wavelengths.

The source/detector 82 may process the reflected radiation to form one or more spectra associated with the sample. The source/detector 82 may also, by executing various statistical routines such as partial least squares regression, derive various sample properties such as chemical concentrations and/or physical, mechanical, rheological, and/or melt properties of components of the sample. Alternatively, the source/detector 82 may provide the reflected radiation data or spectra to a workstation 56 or computer, for further processing.

The source/detector 82 may incorporate an optical grating through which the reflected radiation is passed to increase spatial resolution within a desired range of wavelengths. For example, an 1,800 line per mm grating increases spectral resolution over the range of 200 to 1,600 $cm^{-1}$, allowing greater discrimination of the crystalline and amorphous bands observed for polyolefins, such as polyethylene.

The workstation 56 may be configured to control the activities of the source/detector 82. The workstation 56 may be connected to other processor-based systems, such as one or more remote computers 92 and may comprise part or all of a distributed control center. The distributed control center may receive data from one or more source/detectors 82, each monitoring different stages of the polyolefin production process. It is to be understood that the connections between the various source/detectors 82, workstations 56, and/or remote computers 92 may be accomplished by various means including wired and wireless connections.

Figure 5:
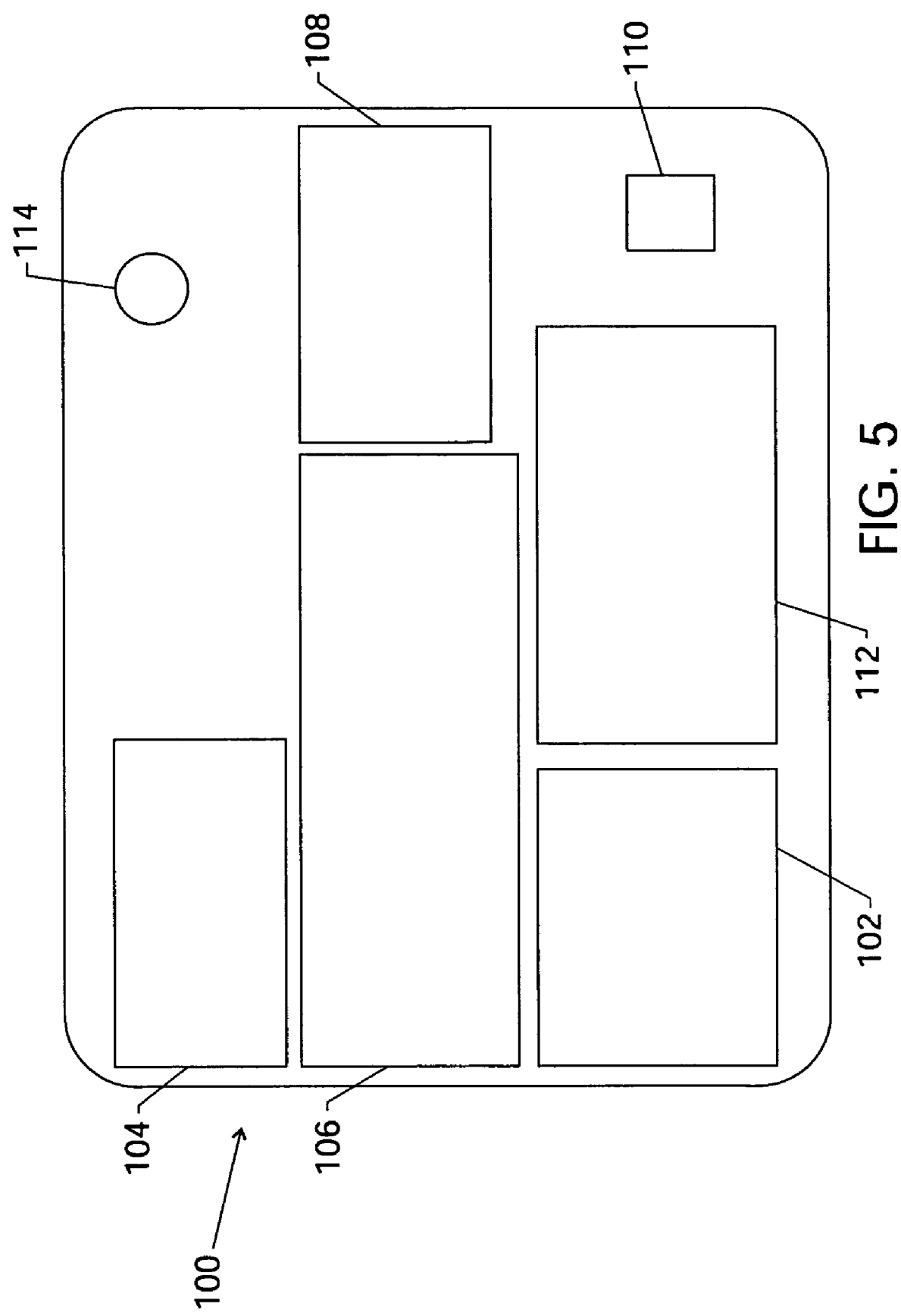
FIG. 5 is a block diagram depicting the components of a portable Raman spectrographic system in accordance with one embodiment of the present techniques.

Though the above description assumes a large or static implementation of a Raman spectroscopic system, portable implementations of Raman spectrometry may also be possible. Referring to FIG. 5, a portable implementation of a Raman spectrometry system is depicted. The portable spectroscope 100 may include a battery pack or power supply 102, a radio link 104 or wireless network module, and a portable source/detector 106. The source/detector 106 may be adjacent to a sample chamber 108 which may be opened to introduce sample and closed to eliminate light contamination during operation. In addition, a processor 110 may be present to execute calibration and monitoring routines stored on a memory device 112. The memory device 112 may comprise an optical or magnetic media, such as a CD, flash RAM, hard disk, or floppy disk. The processor 110 may also control communication between the radio link 104 or network module and a remote database or network. An operator interface 114 may also be present on the portable spectroscope 100 to allow an operator 58 to activate the unit 100 or initiate a measurement.

b. Probe Design

While Raman spectrometry provides advantages in the detection and quantification of the reactants, products, and/or product properties during polyolefin production, many of the production environments may damage the exposed equipment, notably the probe, or otherwise impair measurements. For example, process environments may expose a probe to extreme temperatures and/or pressures as well as to caustic agents and/or various particulate adherents. The probe may therefore incorporate various features to improve survivability and/or facilitate operation in the process environment. For example, referring to FIG. 6, a probe tip 120 is depicted which includes a curved or ball lens 122 which is suitable for use in environments where particulate buildup is likely. The lens 122 is secured within a lens housing 124 in the probe tip 120 which may comprise a lens sleeve 126 sized to accommodate the circumference of the lens 122. The lens 122 may be secured within the opening, such as by a suitable adhesive or by brazing with silver or another suitable material. In the depicted embodiment a braze seal 128 is provided. In addition, a secondary seal 130 may be provided to further exclude the environment, such as dust and moisture from the probe tip 120. The secondary seal 130 may include a window 132 transparent to the wavelengths to be transmitted to and from the probe tip 120. The secondary seal 130 may also include a collimator region 134 which is opaque to the laser and backscatter wavelengths and which helps to focus the laser beam.

Figures 6, 7:
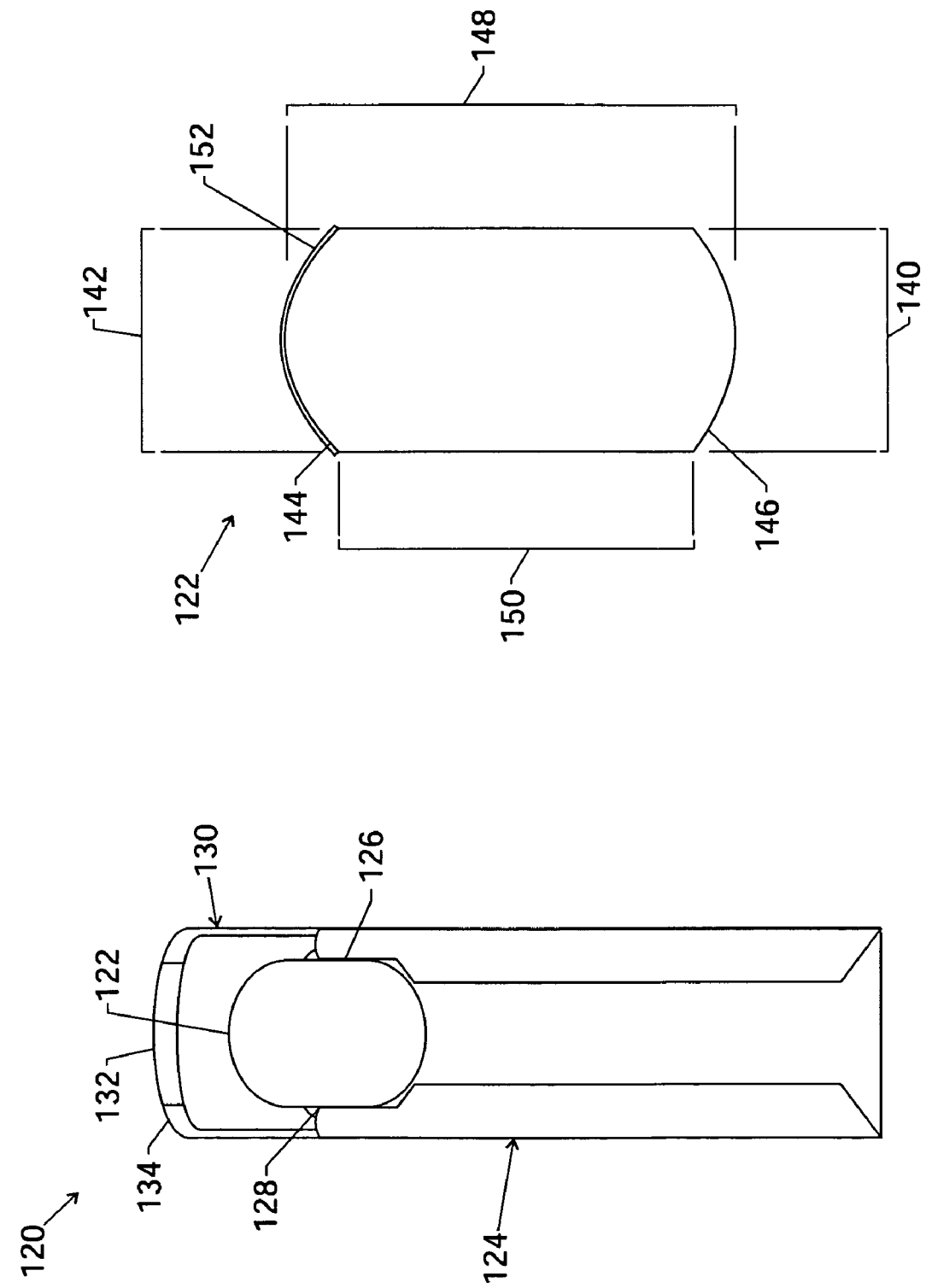
FIG. 6 is a cross-section taken along the axis of an exemplary Raman probe tip in accordance with one embodiment of the present techniques.
FIG. 7 is a cross-section taken along the axis of a sapphire lens for use in a Raman probe in accordance with one embodiment of the present techniques.

The curved lens 122 may be constructed from sapphire, diamond or other suitable materials, i.e., materials which transmit the desired light wavelengths. For example, in one embodiment, a sapphire lens 122 is employed which is capable of withstanding up to 15,000 p.s.i.g. and which has an approximately 2 mm focus point. Referring to FIG. 7, the lens 122 is seen in greater detail. In particular, it can be seen that the lens 122 possesses a minimum diameter 140, for insertion in the cylindrical sleeve 126, and a maximum diameter 142. In one embodiment, the minimum lens diameter 140 may be between 4.4 mm and 4.6 mm and the maximum lens diameter 142 may be between 4.6 mm and 4.9 mm. In addition, the lens 122 has an exposed curvature 144 on the end which may contact the medium being sampled and an unexposed curvature 146 on the end interior to the probe tip 120. Because of the curvatures 144 and 146, the lens has two different lengths which may be defined, a total length 148 and uncurved length 150. The total length 148 comprises the length of the lens 122 along its longest axis, i.e., from the apex of the exposed curvature 144 to the apex of the unexposed curvature 146, and in one aspect of the present technique may be between 9 mm and 10 mm. The uncurved length 150 comprises the length between the curvatures 144 and 146 and in one aspect of the present technique may be 7 mm and 7.5 mm. In one embodiment, the exposed curvature 144 is coated with an anti-reflective coating 152 to improve performance by reducing the transmission of incidental scatter.

Figure 8:
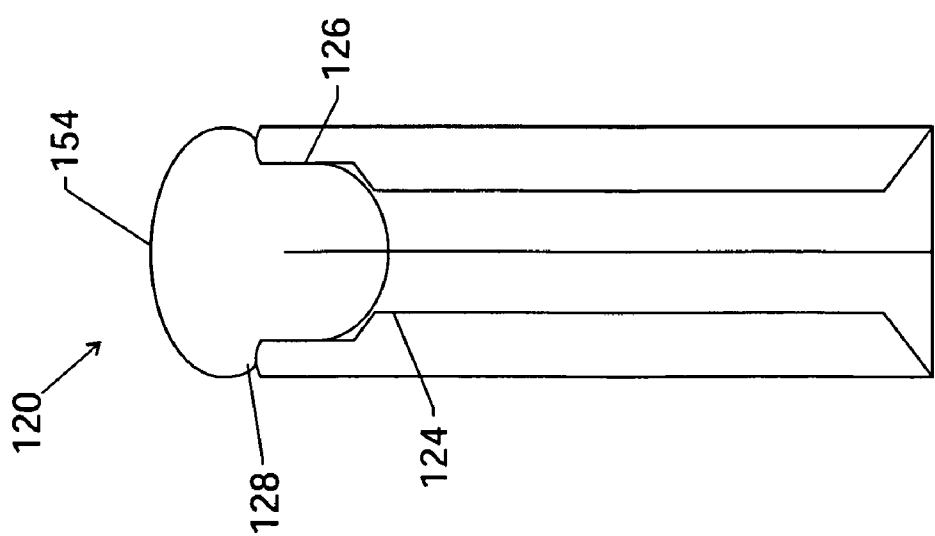
FIG. 8 is a cross-section taken along the axis of a Raman probe tip housing a mushroom-shaped lens in accordance with one embodiment of the present techniques.

The use of spherical or curved lenses 122 may prevent fines or other particulates from adhering on the surface of the lens 122 and indeed may be self-cleaning in a flowing medium. The spherical or curved lens 122 may be configured with a constant focus and may therefore be used without the focusing optics associated with flat lenses, such as a focal rod. Alternatively, as depicted in FIG. 8, a mushroom-type lens 154, as opposed to a ball type lens 122, may be incorporated into the probe tip 120, providing similar advantages.

Figure 9:
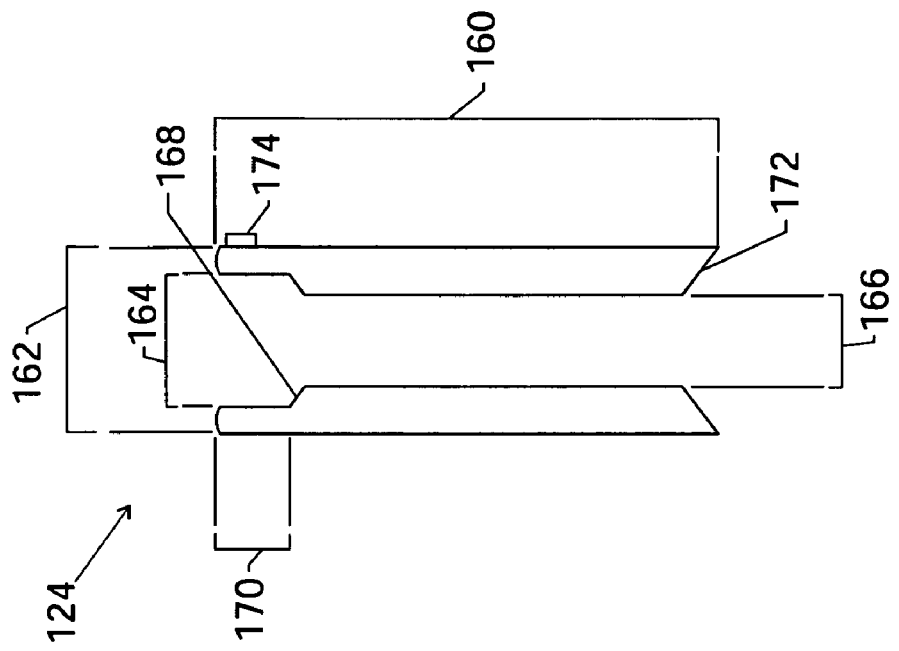
FIG. 9 is a cross-section taken along the axis of a Raman probe tip for housing a lens in accordance with one embodiment of the present techniques.

A probe tip 120 which accommodates the lens 122 or 154 is depicted in greater detail in FIG. 9. The lens housing 124 has a length 160, which in one aspect of the present technique may be between 2 cm and 3 cm, as well as an outer diameter 162, which may be between 9 mm and 10 mm. The housing 124 may have two interior diameters, a lens inner diameter 164, associated with the lens sleeve 126, and a fiber inner diameter 166, sized to accommodate a fiber optic cable 86. In one aspect of the present technique, the lens inner diameter 164 may be between 4.75 mm and 5.25 mm and the fiber inner diameter 166 may be between 4.0 mm and 4.5 mm. The region connecting the inner diameters 164 and 166 may comprise a bevel 168, such as a 35° to 60° bevel. A sleeve length 170 may be defined as the region of the sleeve 126 between the bevel 168 and the end of the housing 124 and, in one aspect of the present technique, may be between 4.75 mm and 5.5 mm. In addition, the housing 124 may include a connection bevel 172, such as a such as a 35° to 60° bevel, to accommodate a fiber optic connector 88 or mating surface connected to the housing 124. The probe tip 120 may also incorporate a thermocouple 174 to measure temperature at the tip 120.

C. Probe Incorporation

The properly configured probe 84 must, of course, be situated in the sample environment 70, such as a production environment, to collect spectra. Insertion of the probe 84 into controlled environments, such as into a reactor, an extruder, a recovery system, or the various piping, tubes and/or conduits associated with polyolefin production, may require a variety of insertion/retraction systems 180. In particular, the insertion/retraction system 180 for a production environment should allow easy insertion and retraction of the probe 84 into the environment 70 without perturbing the environment 70 or allowing material to flow between the production and non-production environments.

Figure 10:
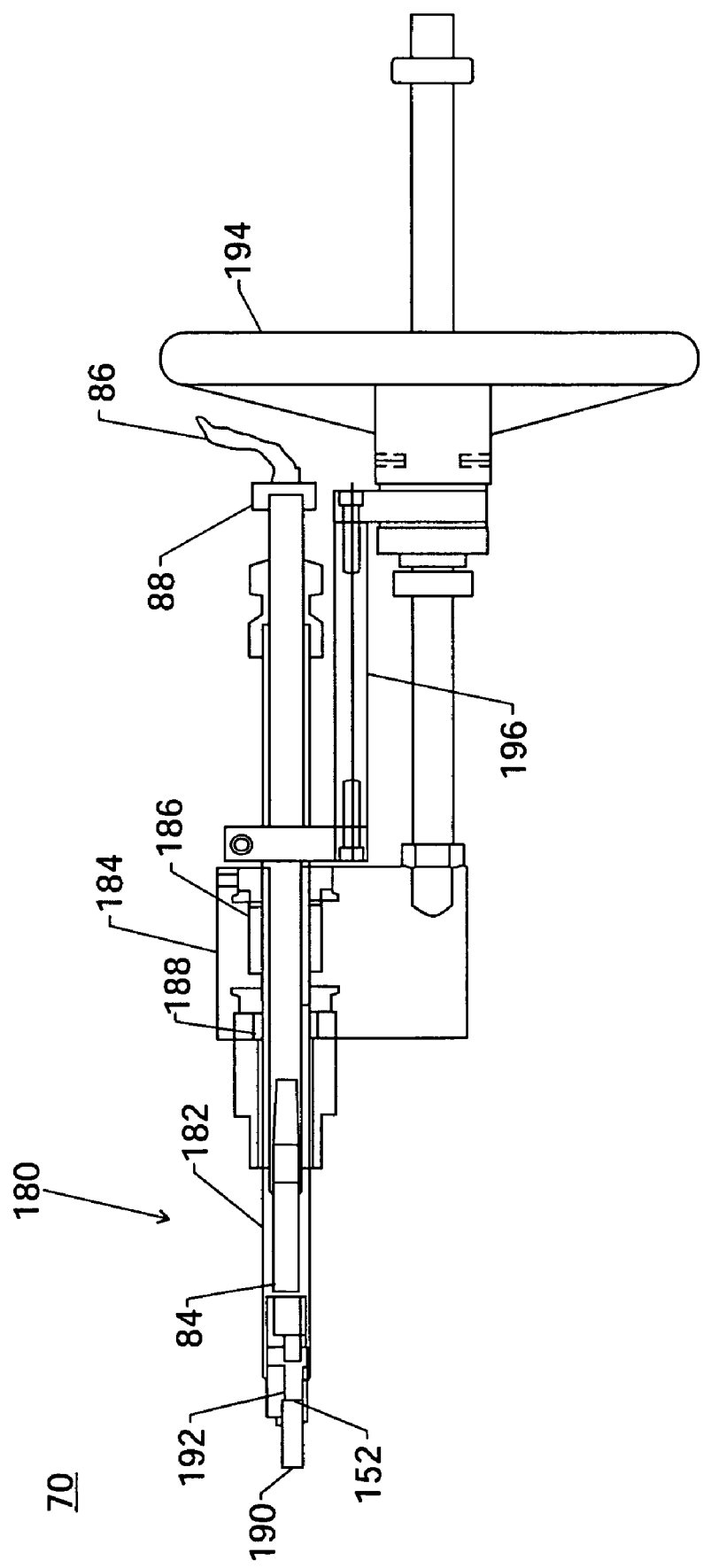
FIG. 10 depicts an insertion/retraction apparatus for inserting a Raman probe into a reaction chamber in accordance with one embodiment of the present techniques.

For example, an insertion/retraction system 180 configured to situate a Raman probe 84 into a reactor or other controlled environment 70 is depicted in FIG. 10. As depicted the probe 84 may be encased in a protective sheath 182 which extends from a reactor wall 184 (184 depicted in FIG. 10 is not the reactor wall, rather it is the probe seal housing). Various seals 186 and bushings 188 may hold the probe 84 securely within the wall 184 while maintaining the controlled environment 70. Additional seals 186 may be present to maintain the controlled environment 70 if the probe 84 is retracted during on-line operation. In addition, primary and secondary probe seals 190 and 192, may be present around the probe tip 120 to protect the lens 122 and to prevent leakage of water or reactants into the tip 120. Indeed, optical elements may be designed to fit within the secondary seal 192 which would allow the lens 122 to be removed from the probe tip 120 without fear of leakage of the sample medium into the probe 84. The secondary seal 192 may be coated with an anti-reflective coating 152, as discussed in regard to the lens 122 above, to improve performance. The probe 84 is attached to a rotary handle 194 by a connector rod 196 which allows the probe 84 to be moved by operating the handle 194. In particular, in the depicted embodiment, the probe 84 may be inserted or retracted through the seals 186 and bushings 188 in the chamber wall 184 by turning the attached handle 194.

The rotary handle 194 allows insertion and retraction of the probe 84 to be performed at a controlled speed and alignment.

The depicted embodiment is suitable for insertion and retraction of a probe 84 into a hostile controlled environment 70, such as the interior of a polymerization reactor or monomer recovery system. However, other controlled environments 70 which operate at less extreme temperature and pressure may incorporate fewer of the depicted features. For example, in an extruder environment, though operating at high temperature and pressure, the probe 84 may be situated above the melt as opposed to immersed within the sample medium. As a result, the protective sheath 182 and lens seals 190 and 192 may be absent. Similarly, within conduits or piping transporting feedstock or feed streams, the environment 70 may be at an ambient temperature and/or at less pressure than in a reaction environment. In such an environment 70, the one or more seals 186 and or bushings 188 may be reduced in strength or may be absent. Other production environments 70 may be substantially uncontrolled in terms of temperature and pressure, such as in polyolefin storage bins or silos or above the extruder feed stream. In such an environment, seals 186 may be reduced or absent as might the controlled insertion and retraction mechanism 194 and 196.

As evidenced by these examples and as will be understood by those skilled in the art, the type and number of seals 186 and bushings 188, the presence or absence of a protective sheath 182, and the presence or absence of a controlled insertion/retraction mechanism 194 and 196 may be determined based on the environment 70 to be sampled. In general, the greater the temperature and pressure differentials and the greater the exposure of the probe 84 to the sample and/or particulates in the sample, the greater the need for the protective or ruggedizing measures such as those depicted.

d. Calibration

Figure 11:
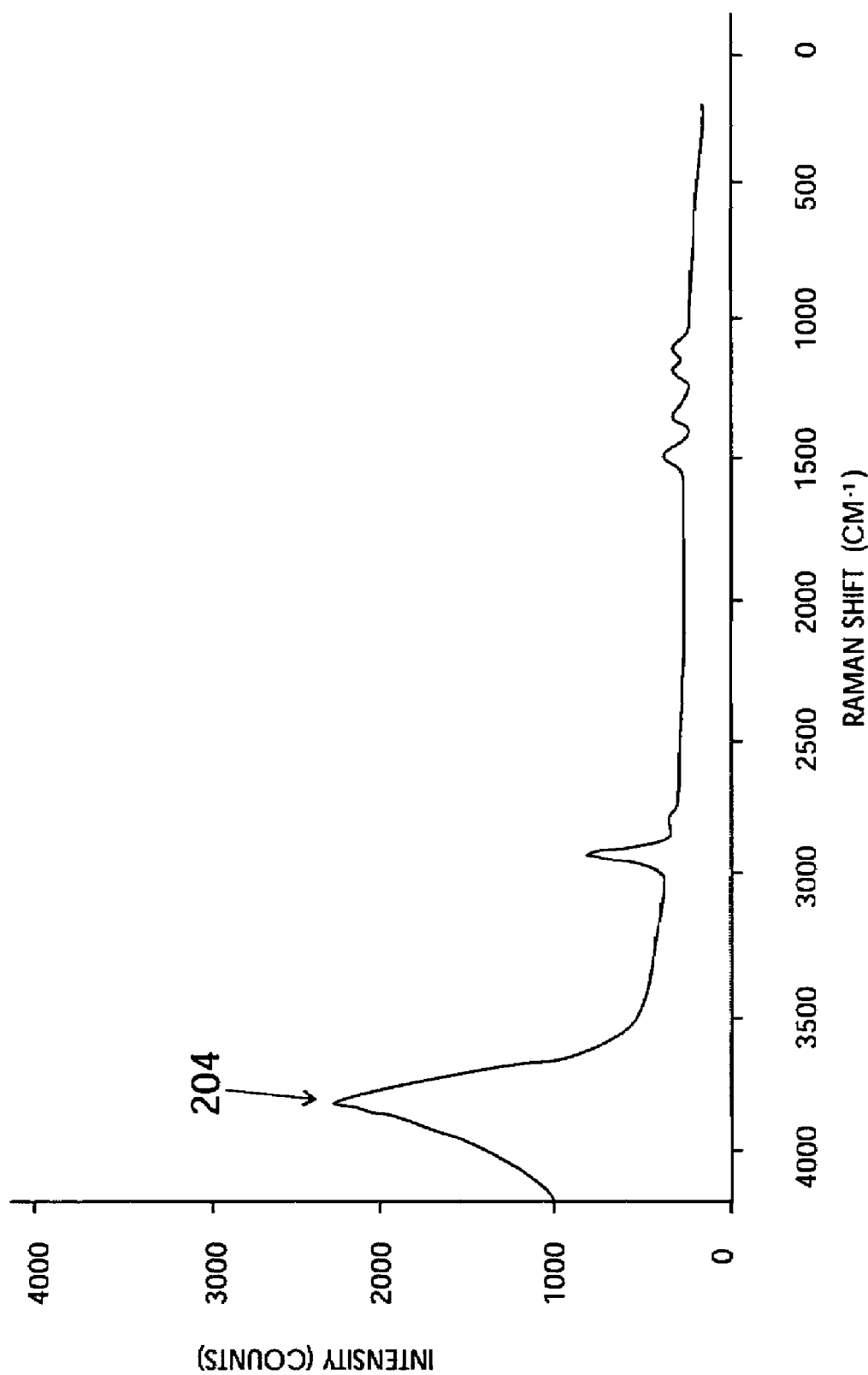
FIG. 11 depicts a Raman spectrum for use in calibration in one embodiment of the present techniques.

In addition to configuring a suitable Raman probe and insertion/retraction system 180, the probe 84 and the source/detector 82 are typically calibrated to provide consistent Raman shift and intensity responses in the acquired spectral data 202, referring to FIG. 11. For example, one method of calibrating a 532 nm Raman spectrometer uses naturally occurring spectral bands 204, which may be observed when a spherical sapphire lens is used in the probe. The naturally occurring spectral band 204 appears in the 3,500-4,100 $cm^{-1}$ region. The location and intensity of the band 204 provides an internal calibration standard, allowing calibration of the x-axis and y-axis, respectively, of the spectrum. Calibration checks of the source/detector and probe may be performed continuously and automatically, such as by an automated routine.

Figure 12:
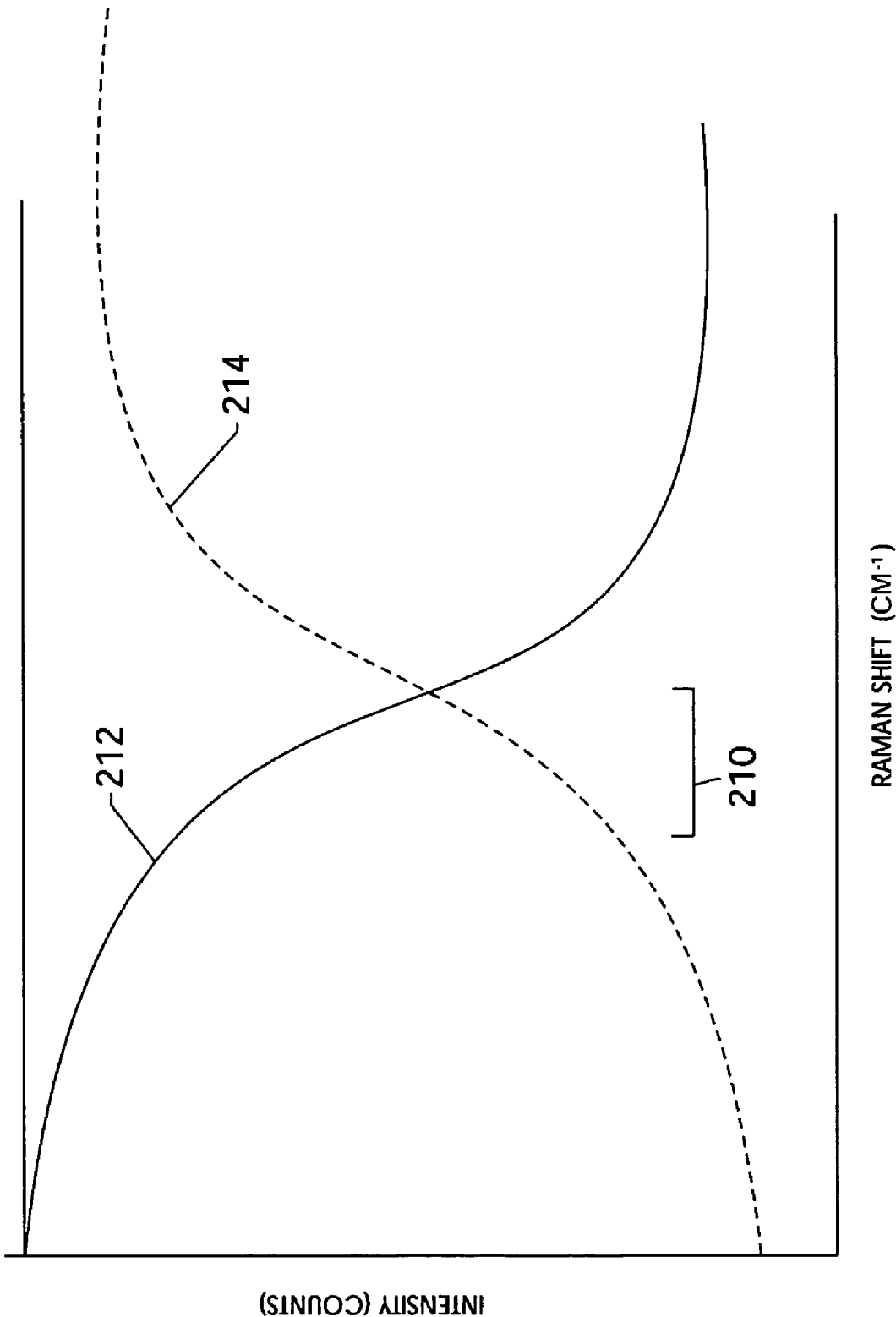
FIG. 12 depicts two filtered Raman spectra for use in calibration in one embodiment of the present techniques.

Similarly, calibration may be performed by measuring the intensity and location of the silicon-oxygen (Si—O) Raman band produced by the optical fiber 86. Referring to FIG. 12, the Si—O band may be isolated in the overlap region 210 of a laser band pass filter spectrum 212 of approximately 785 nm and a shifted spectrum edge filter spectrum 214. In particular, in the overlap region 210, some laser radiation excites the Si—O Raman band. The selection of the edge filter limit for passing shifted radiation back to the source/detector 82 allows a small, quantifiable, and consistent Si—O band to be observed at a fixed frequency which may be used for calibration. Calibration checks of the source/detector 82 and probe 84 may also be performed continuously and automatically by an automated routine using the Si—O band.

Figure 13:
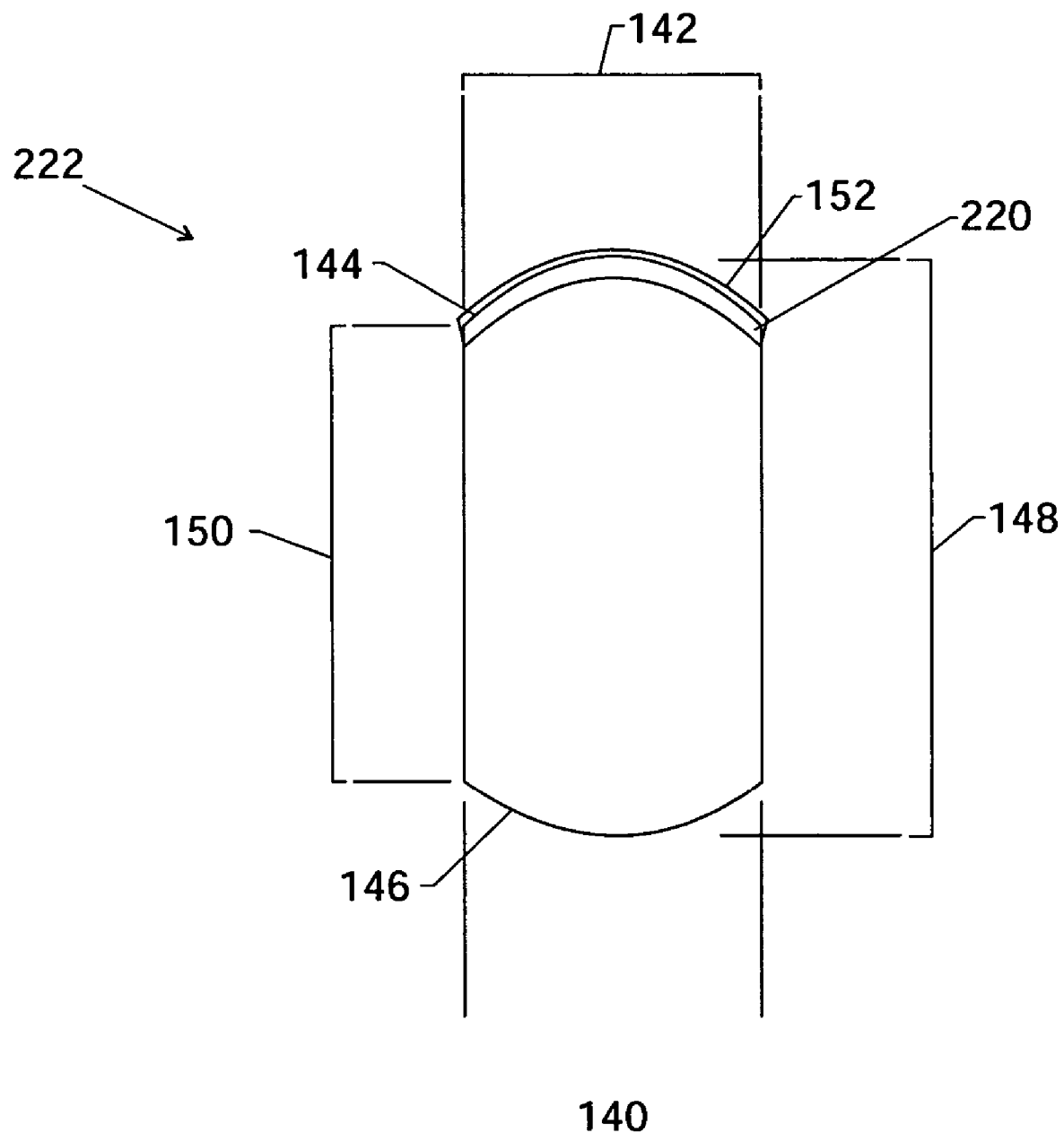
FIG. 13 is a cross-section taken along the axis of a sapphire lens incorporating a spinel material for use in a Raman probe in accordance with one embodiment of the present techniques.

Alternatively, a lens 122 may be utilized which incorporates a material which superimposes a distinct spectral signature with the other lens materials, typically diamond or sapphire. For example, in one embodiment, a spinel material 220 may be combined with sapphire or diamond to form a lens 222 incorporating a calibration matrix, as depicted in FIG. 13. The spinel material 220 may be of varying thickness and shape. The spinel material's broad band fluorescence signature along with the probe and/or sapphire lens peaks can be used as a reference spectrum for both x-axis and y-axis calibration for every spectrum taken, thus eliminating the need for calibration verification. The signature may be used to calibrate the combination of any probe 84 and source/detector 82.

Figure 14:
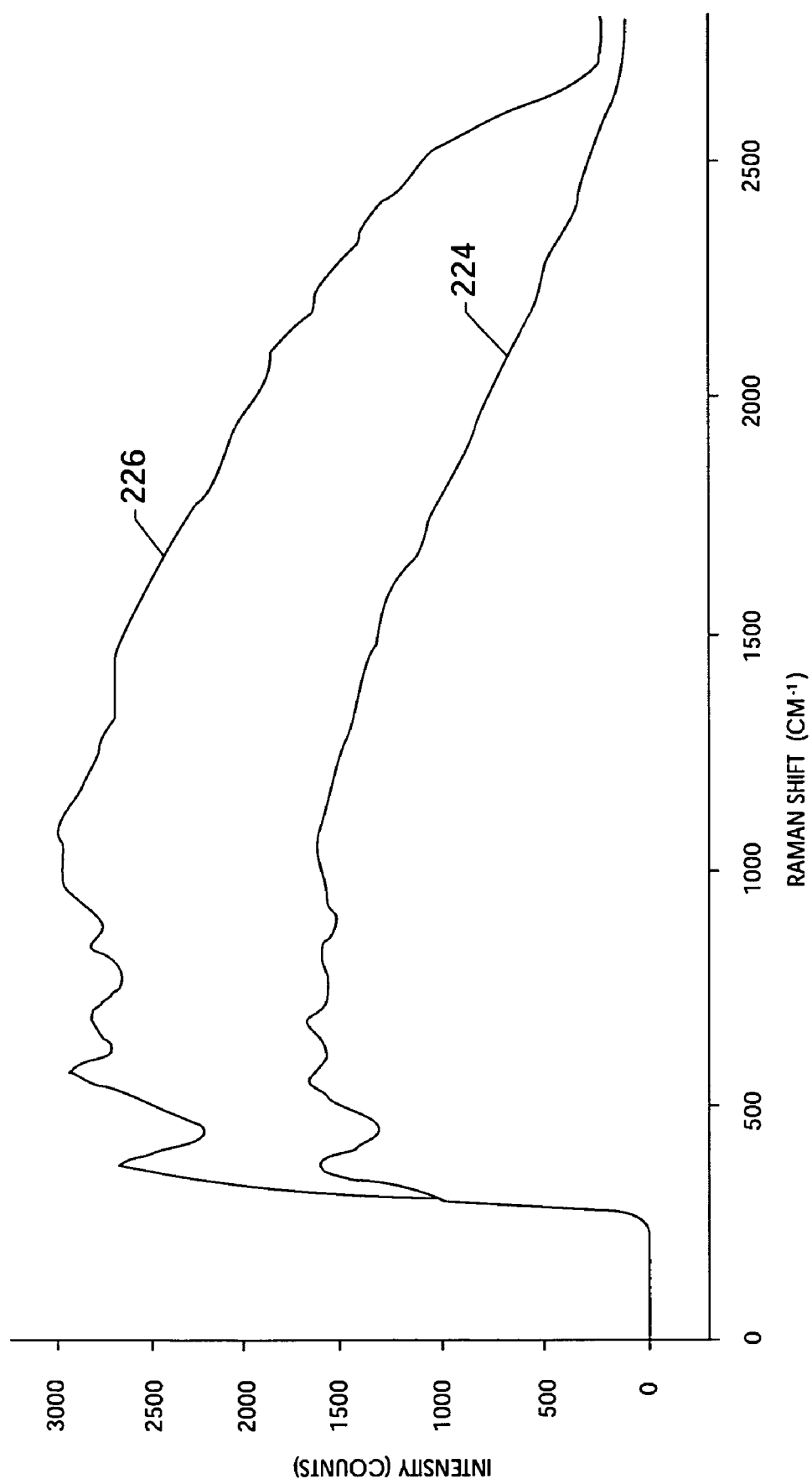
FIG. 14 depicts a Raman spectrum from a spinel lens and a white light spectrum in accordance with one embodiment of the present techniques.

For example, referring to FIG. 14, a spinel broad band fluorescence signature 224 obtained using a lens 222 incorporating a spinel material 220 is depicted along with a diffuse white light signature 226 of the type typically used for taxis calibration. The spinel spectrum was obtained using a 785 nm laser. The spinel signature 224, as can be seen, shows the same characteristics as the white light signature 226. The spinel signature 224 also shows the same characteristics as the chromium fluorescent glass proposed by the National Institute of Standard and Technology for y-axis, i.e., intensity, calibration. The combination of x-axis and y-axis calibration for every spectrum acquired by a probe tip 120 in contact with the sample provides constant and uniform calibration. In particular, calibration of the entire optical path of the light, as accomplished by this technique, is very desirable for calibration in a production environment.

Figure 15:
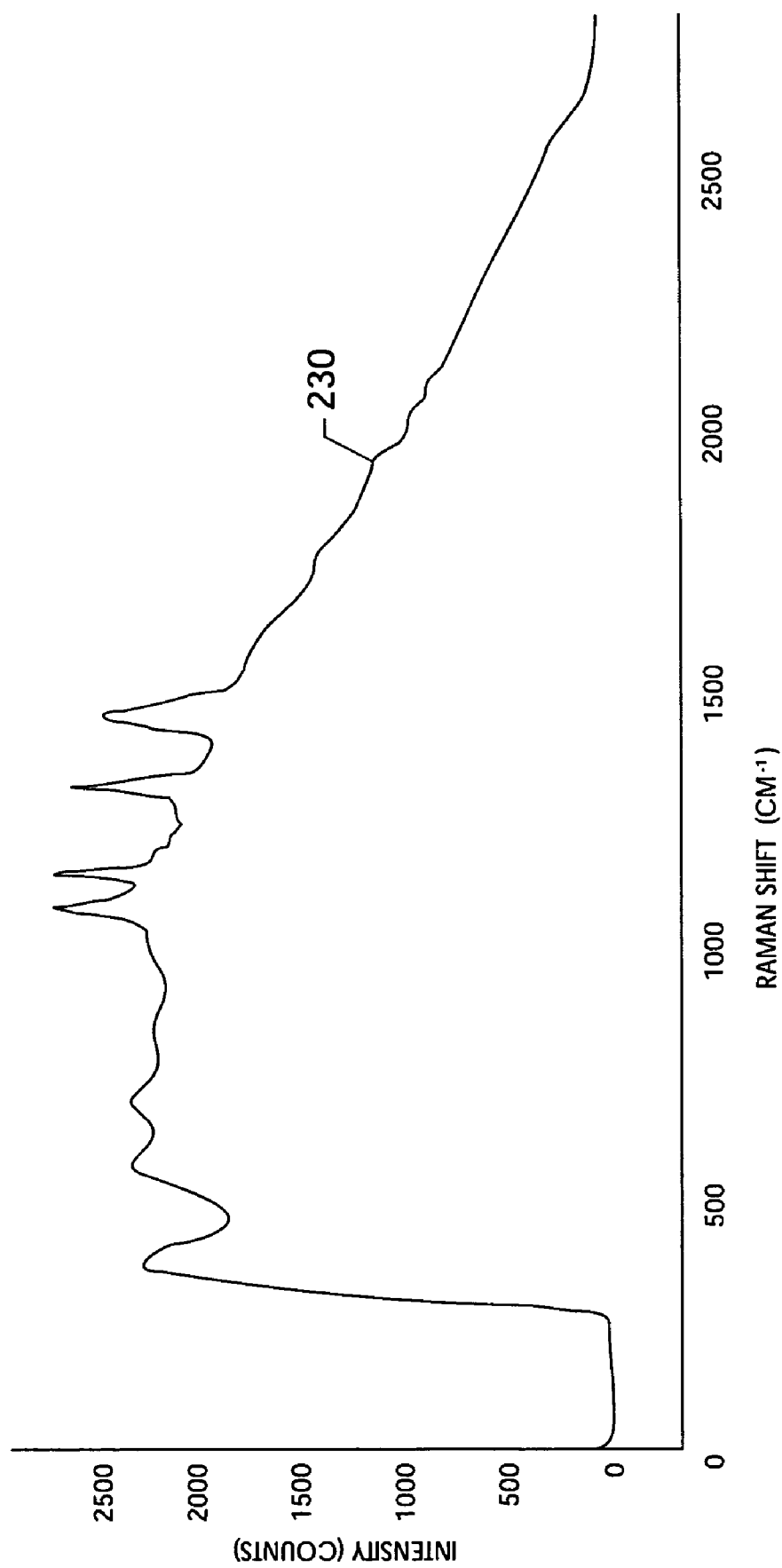
FIG. 15 depicts a Raman spinel spectrum combined with the spectrum from a polyethylene sample in accordance with one embodiment of the present techniques.
Figure 16:
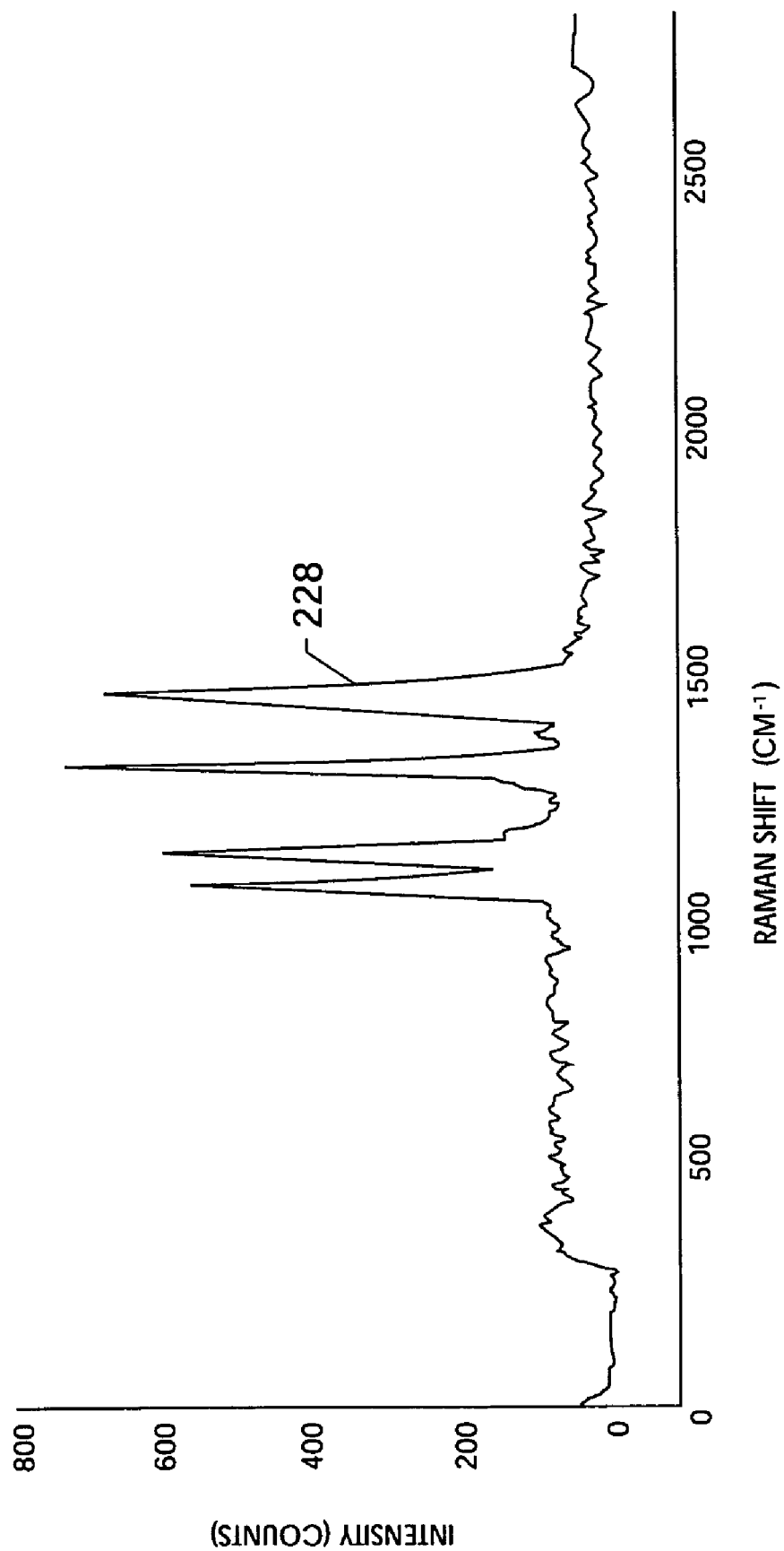
FIG. 16 depicts the Raman polyethylene spectrum after subtraction of the spinel spectrum in accordance with one embodiment of the present techniques.

In this example, the spinel signature 224 is added to the sample spectrum 228 during sample imaging to yield a combined spectrum 230. The combined spectrum 230 depicted in FIG. 15 is representative of a polyethylene spectrum added to the spinel signature spectrum 224 as measured through a 7.5 mm diameter spinel and sapphire ball lens. Subtraction of the spinel signature 224, as depicted in FIG. 16, provides calibration intensity and wavelength of the data and allows a clean sample spectrum 228 to be obtained for analysis.

Alternately, diamond and sapphire may be incorporated as probe components to provide wavelength and intensity calibration during each scan. Diamond and sapphire may both be used for wavelength calibration, generating peaks at known wavelengths. In addition, diamond may be used for intensity calibration, providing predictable counts. In particular, a diamond component 234 may be used in conjunction with a sapphire lens 122, such as a ball lens, to provide an intensity calibration during each scan.

Figure 17:
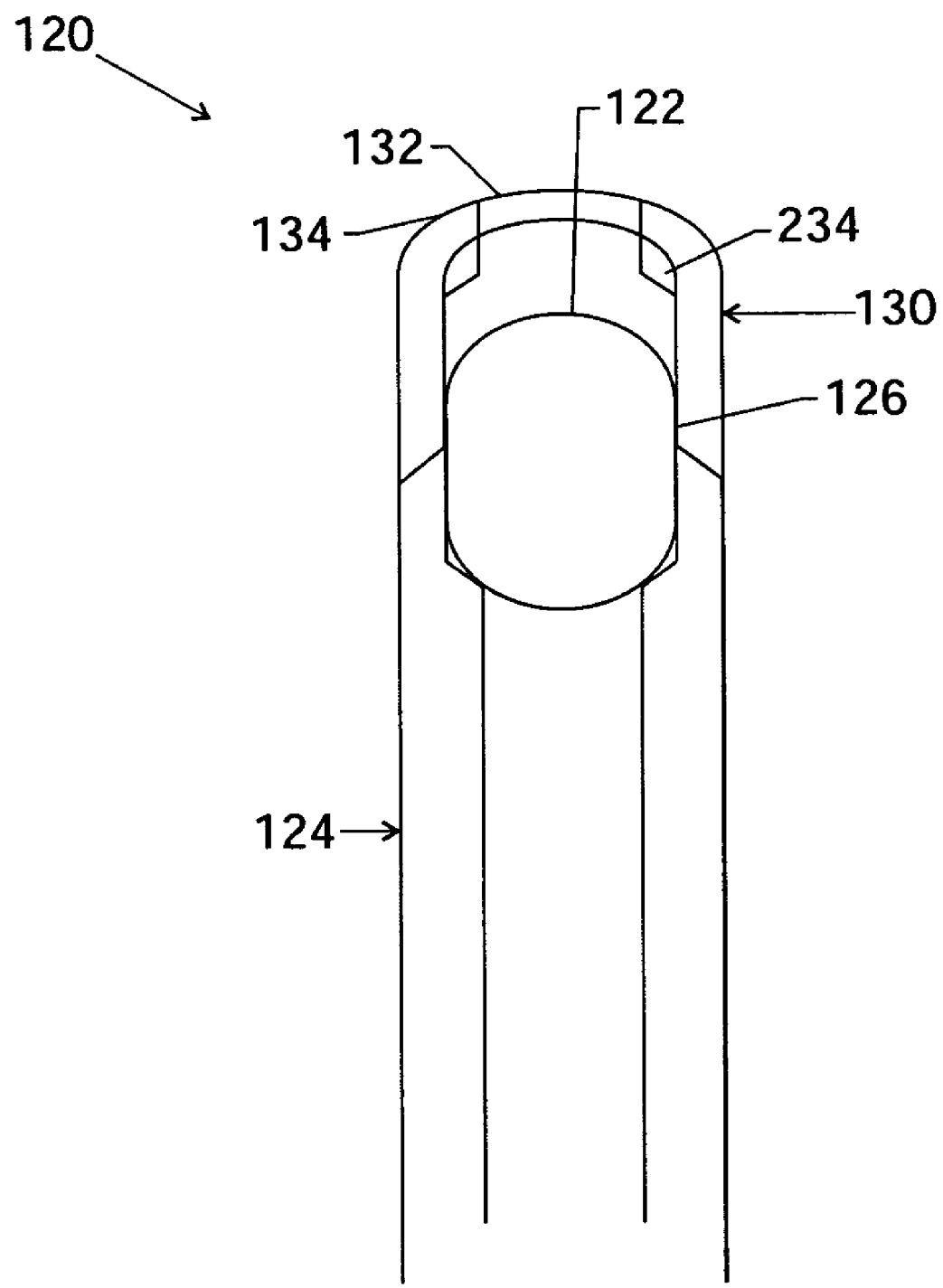
FIG. 17 is a cross-section taken along the axis of an exemplary Raman probe tip incorporating a diamond component in accordance with one embodiment of the present techniques.

For example, referring to FIG. 17, a diamond 234 or diamond window situated in the collimated portion of the laser beam may provide a suitable signal for intensity calibration, as opposed to other configurations which may provide too large a signal for calibration purposes. The diamond and/or sapphire signals may also be used for wavelength calibration, providing good x-axis and y-axis calibration during each scan. Additionally both the sapphire 122 lens and the diamond component 234 or window may be constructed to provide primary and secondary seals 190 and 192 within the probe tip 120 to protect the probe optics from the sample environment 70, such as dust and moisture.

Figure 19:
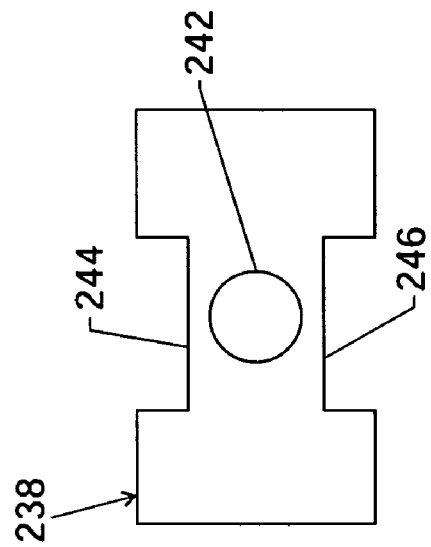
FIG. 19 is a front view of the valve of FIG. 18.
Figure 18:
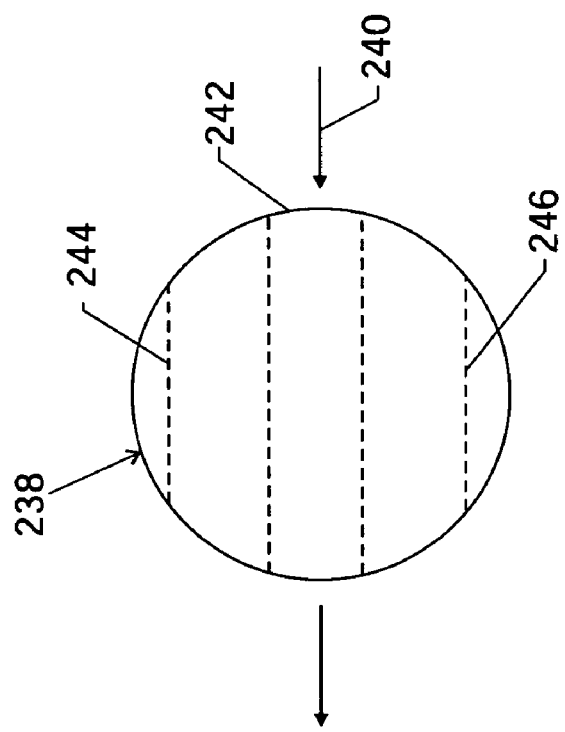
FIG. 18 is a side view of a cylindrical valve for use in calibration in one embodiment of the present techniques.

If other calibration techniques are used, however, verification of the calibration must typically be performed. Verification usually involves taking periodic measurements of known reference materials. One way this may be done is to incorporate a 3-position cylindrical shutter 238, as depicted in FIGS. 18 and 19, in the probe assembly. For example, the shutter 238 may be used to couple the probe 84 to the production process as a closed ball valve, providing an "O" ring seal to protect the probe 84 from exposure to the elements.

The shutter 238, when incorporated into the beam path 240, has three positions, one open and two closed. In the open position, as depicted, the beam passes through an opening 242 transverse to the cylinder. The two closed positions, however, are separated by 180 degrees on the circumference of the cylinder and at right angles to the open path, such that, in the closed position, the beam strikes one of two recessed surfaces 244 and 246. Each recessed surface 244 and 246 is embedded with different solid reference materials, such as low density polyethylene, high density polyethylene, or Teflon. Thus, depending on which closed position is selected, a different reference material is struck by the beam, allowing additional calibration information to be acquired.

e. Measuring Chemical Concentrations

Once calibrated and situated in the sample location, the Raman probe 84 and source/detector 82 may acquire spectral data 202 about the monitored production process. The spectral data 202 may be used, either by the source/detector 82 or by a connected processor-based system 56, to determine the chemical constituents of the sample. In particular, what intensities, i.e., peaks, are present at what wavelengths may be used to determine what chemicals are present in the sample. In the presence of a complex sample, i.e., multiple constituents, statistical analyses, such as least squares partial regression, may be performed on the spectral data 202 to determine the constituents. In addition, the respective concentration of each constituent in the sample may be determined from the sample spectrum using statistical modeling techniques.

Generally, suitable software must be capable of building models between spectral data 202 and concentrations and/or other characteristics determined by some other method and which have a relationship to the spectral response. Such software is typical and commercially available. For example, a chemical concentration in a sample may be determined using a concentration model. The data underlying the concentration model may be acquired from a separate analysis, such as an analysis using a standard with a known concentration. The Raman spectral data 202 or parts of the spectral data 202 resulting from the analysis of the known standard may then be correlated to the known sample concentration and used to develop a concentration model. A concentration model may be created using commercially available software, such as the GRAMS/32 and PLSplus/IQ programs available from Galactic Industries Corporation (Salem, N.H.). The concentration model may be calculated and sample concentrations may be determined, such as with the Galactic GRAMS/32 program.

One may employ additional statistical or computational analysis to confirm or refine the correlation between chemical concentrations and the peaks, i.e., intensities, generated by Raman spectrometry analysis. For example, one may perform partial least squares regression analysis, using the Galactic PLSplus/IQ program. Partial least squares analysis enables the development of a concentration model where one or more components may have some peaks that overlap.

f. Measuring Physical Properties

In addition, properties of the polyolefin itself or percent solids in the sample may be determined using Raman spectrometry at appropriate locations within the production process. For example, using the types of statistical analysis and applications discussed in regard to concentration, statistical models can be constructed using percent solids, physical, mechanical, rheological, and/or melt data from known samples to correlate the polyolefin property of interest with characteristic Raman spectral data 202. The models can then be used to determine the percent solids, physical, mechanical, rheological, or melt properties of the polyolefin in a measured sample. As with the concentration models, additional statistical or computational analyses may be used to refine the models.

For example, in one implementation, chemometric models may be used to determine polyolefin density based on Raman spectral data 202 obtained using a low resolution spectrometer and three absorption peaks in the 690-1129 $cm^{-1}$, one broad peak and two medium intensity peaks. Analysis times are one to eight minutes. The density of polyolefin fluff, melt, or pellets may be measured on-line with a low-resolution (i.e., 15 $cm^{-1}$) Raman Systems R2001. Modifications may include dark current optimization, and x-axis auto-calibration. The statistical model employed may be used to evaluate spectra goodness-of-fit, to reject of outliers, and to correlate the intensities of the sample spectrum with the model spectrum.

Higher resolution Raman Systems R2001 may also be used to measure polyolefin density. In one implementation, an 1,800 line per millimeter grating may be utilized with the Raman source/detector 82 to increase spectral resolution between of 200 to 1600 $cm^{-1}$. The resulting high resolution spectral data 202 provide greater discrimination of crystalline and amorphous bands on the x-axis. Partial least squares regression analysis may then be used to model the physical, mechanical, rheological, and/or melt property of interest and to thereby determine the property from sample spectral data 202.

While density is one polyolefin property that can be determined in this manner, other properties include melt flow rate (MFR), melt index (MI), high load melt index (HLMI), and zero shear viscosity. The full spectral data 202 may be used in determining these properties or, in the case of the 532 nm Raman system, the ratio of C—H stretch to C—C backbone may be related to molecular weight, and thereby to the property of interest. As noted above, this technique may be applied to polyolefin in the fluff, melt, or pellets stages of production. In addition, similar chemometric techniques may be used to determine percent solids at applicable stages of polyolefin production, such as in the reactor subsystem 20, reactor discharge, or polyolefin and monomer recovery systems 24.

B. Control

In response to the data 62 acquired by the monitoring techniques described above, conditions within the production process may be adjusted to produce polyolefin with the desired qualities and characteristics. For example, referring to FIG. 20A, a manual process is depicted whereby a monitor device 54, such as a Raman source/detector 82, provides monitor data 62 to an operator 58, such as via a display device 260 or printed report 262. The operator 58, based upon the monitor data 62, may then adjust 264 one or more production parameters, such as by manually adjusting a production control 266 or by executing a control routine on a workstation 56 or computer to adjust the production control 266. The production control 266 may comprise a variety of controls which, upon adjustment, change one or more production conditions. Examples of production controls 266 include, flow control valves or regulators, compressors, displacement pumps, temperature and/or pressure controls or settings, and speed regulators, such as might control an impeller or paddle inside a chemical reactor.

The monitor data 62 provided to the operator 58 may comprise the unprocessed measured data, such as one or more sets of Raman spectral data 202, and/or processed measured data, such as a chemical concentration or percent solids measurement or a determination of a physical, mechanical, rheological, or melt property of the polyolefin, as determined by chemometric methods such as those discussed herein. Indeed, the monitor data 62 reported to the operator 58 may include a combination of these types of data, such as Raman spectral data 202 along with the various concentrations, percent solids, or polyolefin properties which may be relevant to the stage of the production process being sampled.

Partially automated control schemes are possible as well. For example, referring to FIG. 20B, an operator 58 may receive the monitor data 62, as described above. The operator 58 may provide the data, or a quantitative or qualitative assessment of the data, into a processor-based system, such as an operator workstation 56 or a computer, such as might comprise part of a distributed control center. The workstation 56 may be configured to receive the data 62 and to execute one or more analysis routines on the monitor data 62. Such routines may include one or more Chemometric modeling routines, such as partial least squares regression analysis, as discussed above. The routines may receive other inputs, such as pressure, temperature, or reactant flow data, from other sources. Based upon the monitor data 62 and any other relevant input, the routines may determine, based on their coding, what if any production process adjustments 264 should be made. The routine may then adjust the respective production control 266 or controls, such as via an electrical or pneumatic signal, depending on the type of control 266 to be affected.

Figure 20:
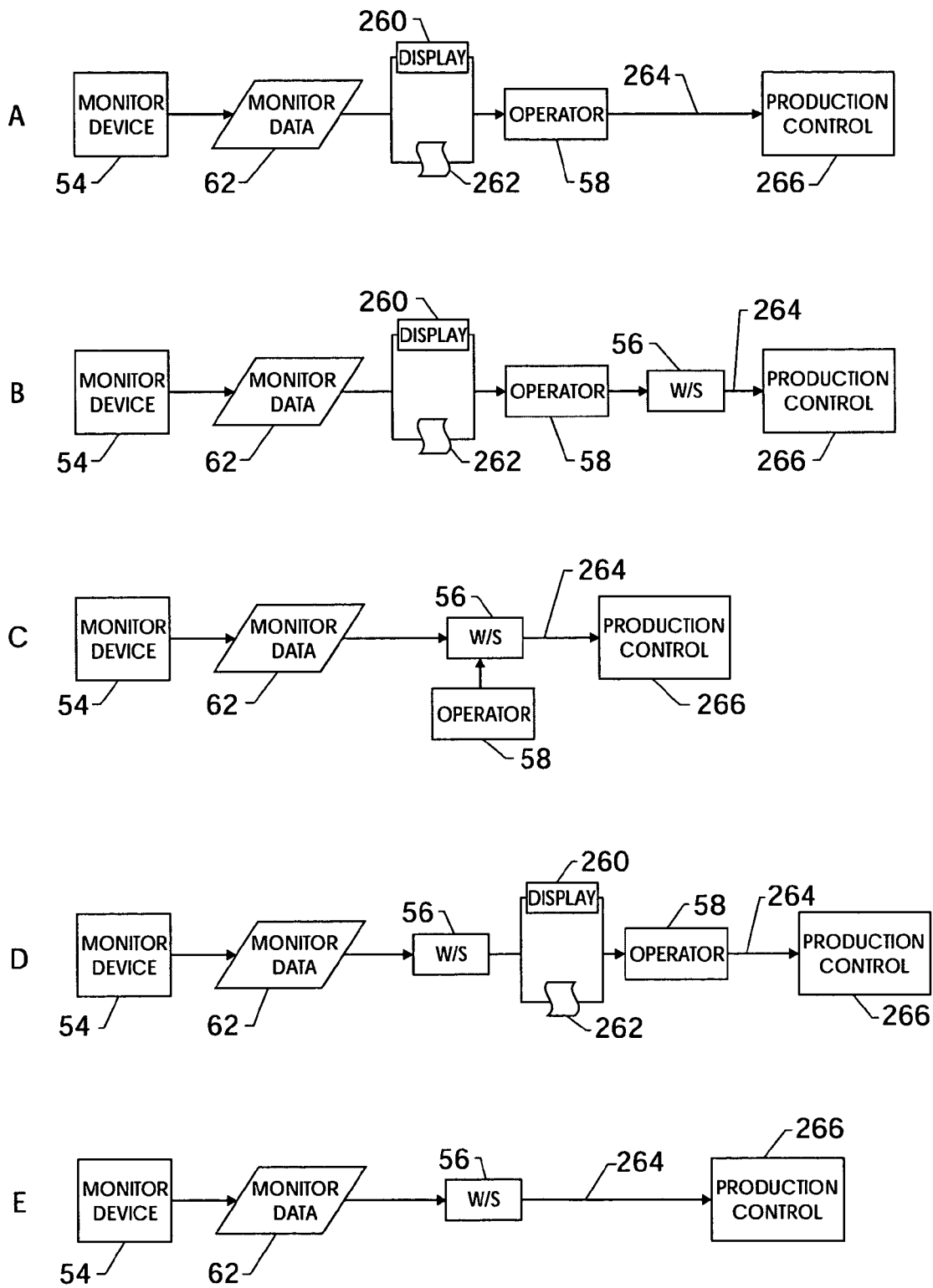
FIG. 20A is a block diagram depicting manual adjustment of a production control in accordance with one embodiment of the present techniques.
FIG. 20B is a block diagram depicting one method of partially automated adjustment of a production control in accordance with one embodiment of the present techniques.
FIG. 20C is a block diagram depicting another method of partially automated adjustment of a production control in accordance with one embodiment of the present techniques.
FIG. 20D is a block diagram depicting another method of partially automated adjustment of a production control in accordance with one embodiment of the present techniques.
FIG. 20E is a block diagram depicting automated adjustment of a production control in accordance with one embodiment of the present techniques.

Alternatively, the workstation 56 may receive the monitor data 62 directly from the monitor device 54 and may initiate the responsive control adjustment 264 at the approval or prompting of an operator 58, as depicted in FIG. 20C. Similarly, as depicted in FIG. 20D, the workstation 56 may receive and process the monitor data 56. Instead of making production adjustments 264 automatically, however, the workstation 56 may display or provide a printed report 262 of the results of the processing, such as recommended actions, to an operator 58 who may make the appropriate adjustments 262 to one or more production controls 266, as discussed above.

Fully automated control schemes may also be implemented, as depicted in FIG. 20E, providing rapid, closed-loop response to deviations from the desired production parameters or product properties. In such a scheme, the monitor data 62 may be received and processed by a workstation 56, as discussed above, which adjusts 264 one or more production controls 266 via electrical or pneumatic signal without operator oversight or intervention.

By these and other responsive control techniques, data 62 from strategically placed monitoring devices 54, such as Raman spectrometers 80, may be used to reduce polyolefin process and product variability. As a result, the production of polyolefin product that possesses the desired physical, mechanical, rheological, and/or melt properties may be facilitated. In addition, production costs may be reduced because of increased reaction efficiency and stability, reduced production of product which is not within a customer's specification, i.e., "off-spec", during grade transitions, as well as the elimination or reduction of lab costs associated with product quality control.

II. EXAMPLES

By way of illustrating implementation of the monitoring and controlling techniques discussed herein, various phases of a polyolefin production process will be discussed with integrated monitoring and/or control mechanisms. The examples provided are not intended to be exhaustive in terms of the stages of polyolefin production, the placement of monitoring devices 54, the properties monitored, or the possible control measures taken in response to the measurements. Instead one skilled in the art will understand that the following examples are merely illustrative of the general principles of the techniques discussed herein and that such principles may be applied in ways which, while not discussed by an example, are within the scope of the invention. Similarly, though Raman spectrometry is discussed in the following examples, one skilled in the art will understand that other monitoring techniques may be utilized, provided that they are capable of providing the monitoring data in the desired time frame and from the desired sample environment.

A. Reactant Supply

One phase of the polyolefin production process which may benefit from the techniques discussed herein is the receipt of one or more reactants from a supplier 14. For example, one or more Raman probes 84 may monitor one or more reactor feedstock components 12 upstream of the reactor feed subsystem 16, such as at a supplier's facility, between the supplier's facility and the reactor feed subsystem 16, or at the entry point to the reactor feed subsystem 16. Spectral data 202 obtained by any one of the Raman probes 84 monitoring the supply streams 12 may be used to determine if contaminants are present and, if so, at what concentrations. For example, Raman spectral data 202 may be obtained for the individual or combined feedstocks 12, such as monomer, diluent, and/or comonomer, and analyzed for the presence of catalyst poisons, such as moisture, carbon monoxide, carbon dioxide, acetylene, and so forth. As one skilled in the art will understand, the greater the sensitivity of the Raman probe 84 and source/detector 82 employed, the smaller the concentration of contaminant or catalyst poison which can be detected.

Detection of contaminants or catalyst poisons in the supplier feedstocks 12 by Raman spectrometry may allow a suitable and timely response to be implemented upstream and/or downstream of the contamination using one or more of the control mechanisms discussed above. For example, the contaminated feedstock 12 may be diverted or terminated in favor of a separate, uncontaminated feedstock 12 prior to delivery to the reactor feed subsystem 16. In addition, upstream conditions may be adjusted to maintain or reestablish an uncontaminated supply of feedstock 12, such as by switching to a fresh monomer treatment bed and/or initiating the regeneration of spent monomer treatment bed. Though monitoring of reactant feedstock has been discussed in the context of polyolefin production, one skilled in the art will readily understand the applicability of such techniques to the commercial production of other chemicals as well.

B. Reactor Feed Subsystems

1. Contaminants

Similarly, Raman spectrometry my be used to monitor for the presence of contaminants, such as catalyst poisons, within the reactor feed subsystem 16 or in the one or more feed streams 18 exiting the subsystem 16. The respective Raman probes 84 may be placed in the conduits or pumping mechanisms of the feed subsystem 16 and may be used to acquire spectral data 202 which may be analyzed to determine not only the presence of a contaminant but also the concentration of such a contaminant.

One or more adjustments 264 may be undertaken in response to a contaminant discovered through this monitoring process, a contaminated feedstock 12 may be diverted or terminated in favor of an uncontaminated feedstock 12. In addition, the pumping operation of the reactor feed subsystem 16 may be diverted or terminated to prevent a contaminated feed stream 18 from reaching the reactor subsystem 20. Notification of the contamination may be sent upstream, such as to a supplier 14, if it is determined that the source of the contaminant is upstream. In this manner, the quality and operability problems associated with contaminants and catalyst poisons in the reactor subsystem 20 may be avoided.

2. Reactants and Coreactants

Figure 21:
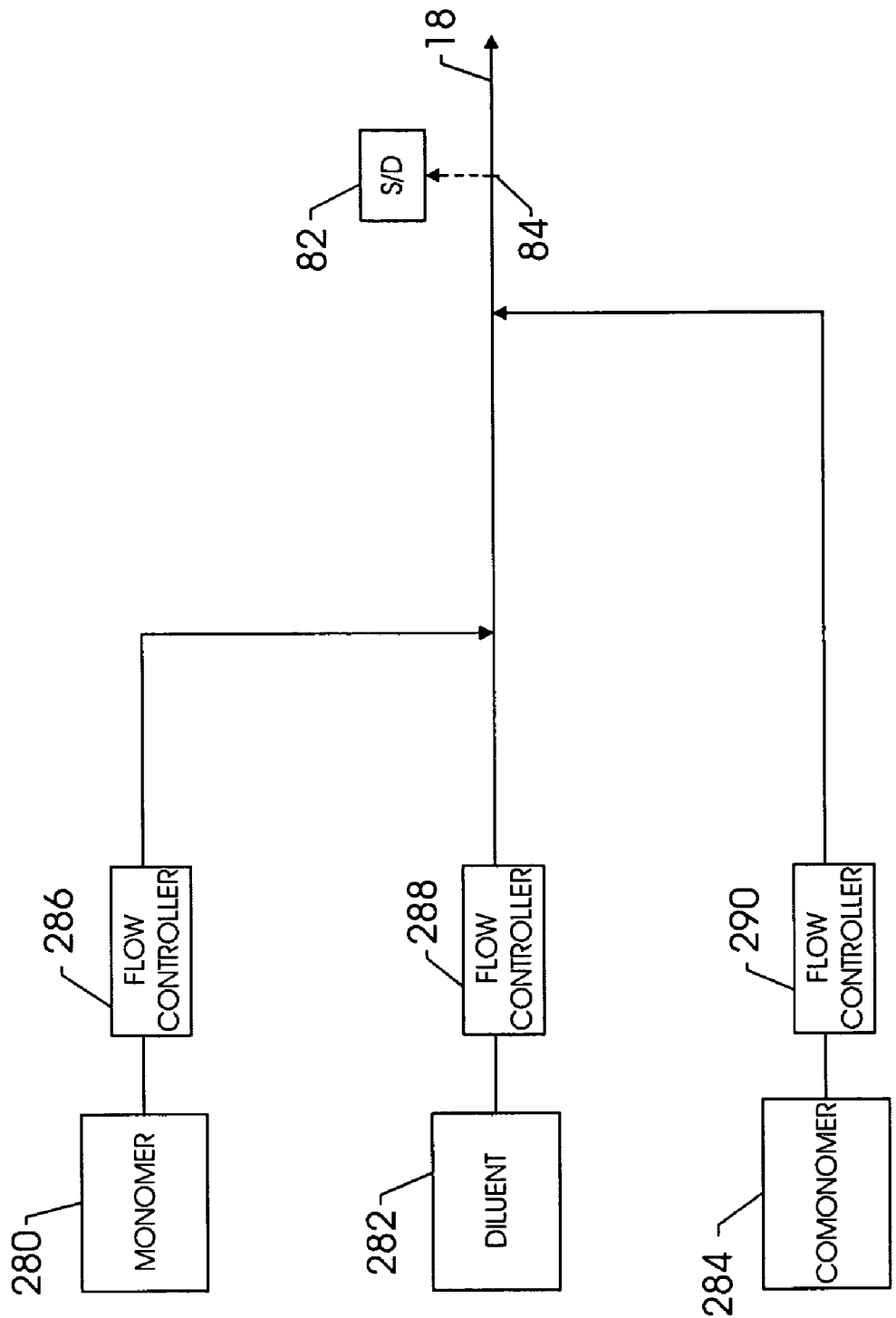
FIG. 21 depicts a reactor feed system including flow controllers and control valves in accordance with one embodiment of the present techniques.

The concentrations and ratios of reactants in the one or more feed streams 18 and in the feed subsystem 16 may also be monitored by Raman spectrometry. In particular, one or more Raman probes 84 may be inserted into the feed subsystem 16 or into the conduit or conduits carrying the one or more feed streams 18 to the reactor subsystem 20. The Raman spectral data 202 obtained by the Raman probes 84 may be analyzed to determine the concentration of one or more reactants or coreactants, such as monomer 280, diluent 282, and/or comonomer 284, as depicted in FIG. 21.

One or more adjustments may be undertaken in response to the measured concentrations. For example, the flow rate of one or more reactants into the feed stream 18 or into the reactor subsystem 20 may be adjusted, such as via a flow controller 286, 288, and/or 290 or flow valve, to obtain the desired concentration or reactant ratio in the feed stream 18 or reactor subsystem 20, as determined by the polyolefin properties which are desired. For example, in polyethylene (PE) production, the concentration of a comonomer 284, such as hexene, in a combined monomer/comonomer/diluent feed stream 18 may be adjusted, by adjusting the flow rate of hexene into the feed stream 18. Such adjustment may be warranted if the concentration of comonomer 284 varies due to fluctuations in the recovered components or from drift in the upstream comonomer flow meter in the reactor feed subsystem 16. The use of Raman spectrometry in the feed stream 18 or the feed subsystem 16 may therefore allow adjustments to be made to reduce or eliminate variability in the comonomer concentration within the reactor subsystem 20, which might otherwise result in variability in the density of the polyolefin produced.

In addition, the use of Raman spectrometry to monitor reactant concentrations in the feed stream 18 and/or the feed subsystem 16 may facilitate adjusting reactant concentrations when so desired. For example, when reactor conditions are changed, such as when a different grade of polyolefin is to be produced, Raman spectral data 202 obtained from within the feed stream 18 and/or the feed subsytem 16 may allow adjustments to be made more rapidly and precisely to the reactant flow rates to obtain the desired reactant concentrations or ratios.

3. Hydrogen

Figure 22:
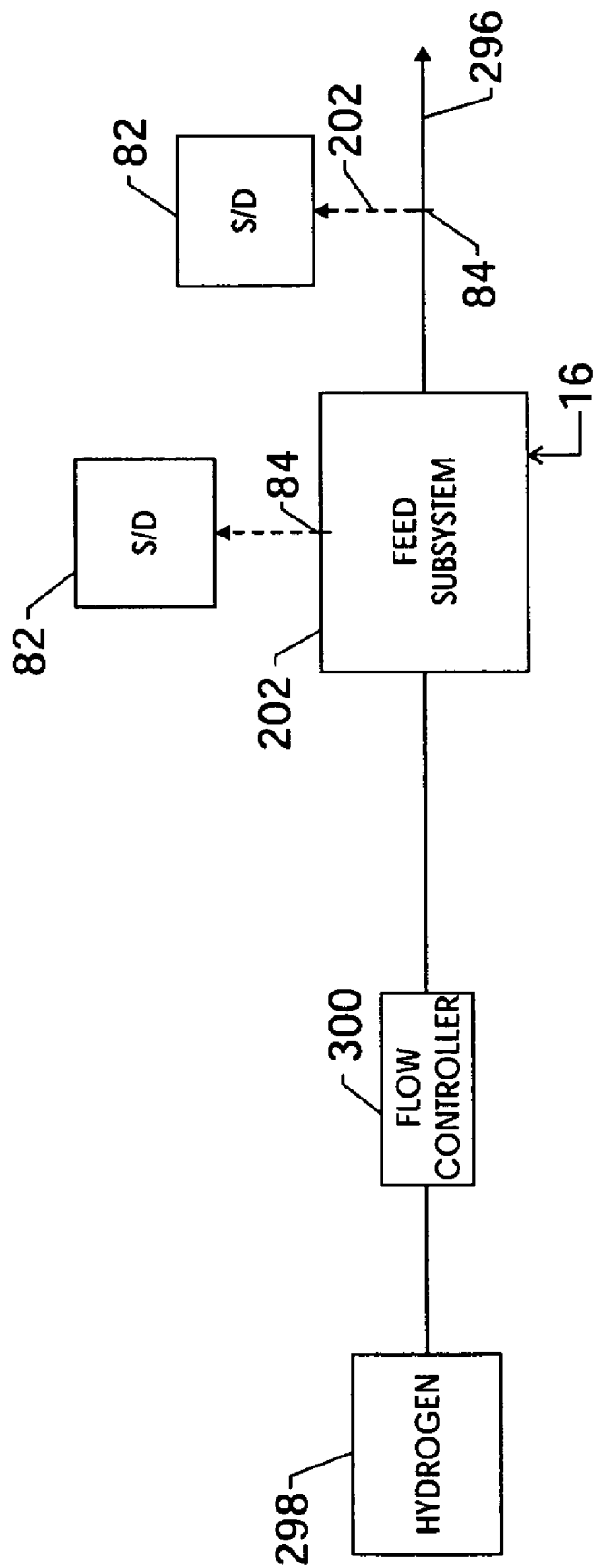
FIG. 22 depicts a hydrogen feed system in accordance with one embodiment of the present techniques.

Hydrogen 298, another typical feed component of polymerization reactions, may determine the fluff properties of the produced polyolefin. In particular, hydrogen 298 may be added to a polymerization reaction as a chain transfer agent, which affects various polyolefin product properties, such as melt flow rate (MFR) and melt index (MI). Therefore, it may be desirable to monitor hydrogen concentration using Raman spectrometry with probes 84 in the reactor feed subsystem 16 and/or in one or more hydrogen feed streams 296 between the feed subsystem 16 and the reactor subsystem 20, as depicted in FIG. 22. In particular, hydrogen concentration may be determined from the obtained Raman spectral data 202.

Based upon the measured hydrogen concentration or the calculated hydrogen flow rate into the reactor subsystem 20, it may be desirable to adjust hydrogen concentration or flow rate based upon the desired polymer properties. For example, in polyproplyene (PP) polymerization, hydrogen concentration in the liquid phase of a loop slurry reactor may be adjusted to control the melt flow rate of the produced PP. The melt index is similarly controlled in PE polymerization processes. To achieve the desired hydrogen concentration, the flow rate of hydrogen 298 from the hydrogen source may be adjusted by operation of one or more flow controllers 300, valves, and/or compressors controlling hydrogen flow into the reactor subsystem 20.

4. Catalysts

The reactor feed subsytem 16 may also supply one or more catalysts 306 and 308 to the reactor subsystem 20 via on or more catalyst feed streams 304. For example, specific catalyst systems for PE polymerization may include single-site metallocene catalysts supported on borate-activated silica, metallocene catalysts supported on an organo-aluminoxy compound, or dual-site chromium catalysts supported on calcined aluminum phosphate. In PP polymerization, some examples are chromium oxide supported on silica oxide ($SiO_2$), titanium chloride (i.e., $TiCl_3$ or $TiCl_4$) supported on either magnesium chloride or silica, or magnesium carbonate ($MgCO_3$) supported on either magnesium chloride or silica. Both PE and PP polymerization may utilize silica-supported metallocene catalysts with methyl aluminoxane (MAO) co-catalysts.

The particles of catalyst 306 and 308 may be diluted in a diluent 282, such as isobutane or mineral oil, in the feed subsystem 16 and fed to the reactor subsystem 20 via a catalyst feed stream 304. For example, referring to FIG. 23, a block diagram depicts an exemplary catalyst feed system 310, which may be a component of the reactor feed subsystem 16. The catalyst feed system 310 may provide a single catalyst 306 or 308 or multiple catalysts 306 and 308, such as metallocene catalysts, to the reactor subsystem 20. Two or more separate catalysts 306 and 308 may be provided by the catalyst feed system 310, typically at a ratio and rate optimized to yield the desired polymerization reaction in the reactor subsystem 20. As depicted, catalysts A 306 and B 308 may be fed to first and second catalyst mix tanks 312 and 314 respectively. Catalyst A 306 and B 308 may be fed to the mix tanks 312 and 314 in a variety of ways. For example, a catalyst 306 or 308 may comprise a slurry which may be fed to the respective tank 312 or 314 via process piping. Alternately, a catalyst 306 or 308 may be provided in the form of dry, solid particles which are manually fed to the respective tank 312 or 314 from catalyst drums. A diluent 282, such as isobutane, may be metered to the mix tanks 312 and 314 to provide a fluid medium for the catalysts 306 and 308. Agitators 316 or recirculating loops (not shown), may mix the catalysts 306 or 308 and diluent 282 to form a catalyst slurry. Catalyst preparation may be a batch process or continuous.

Figure 23:
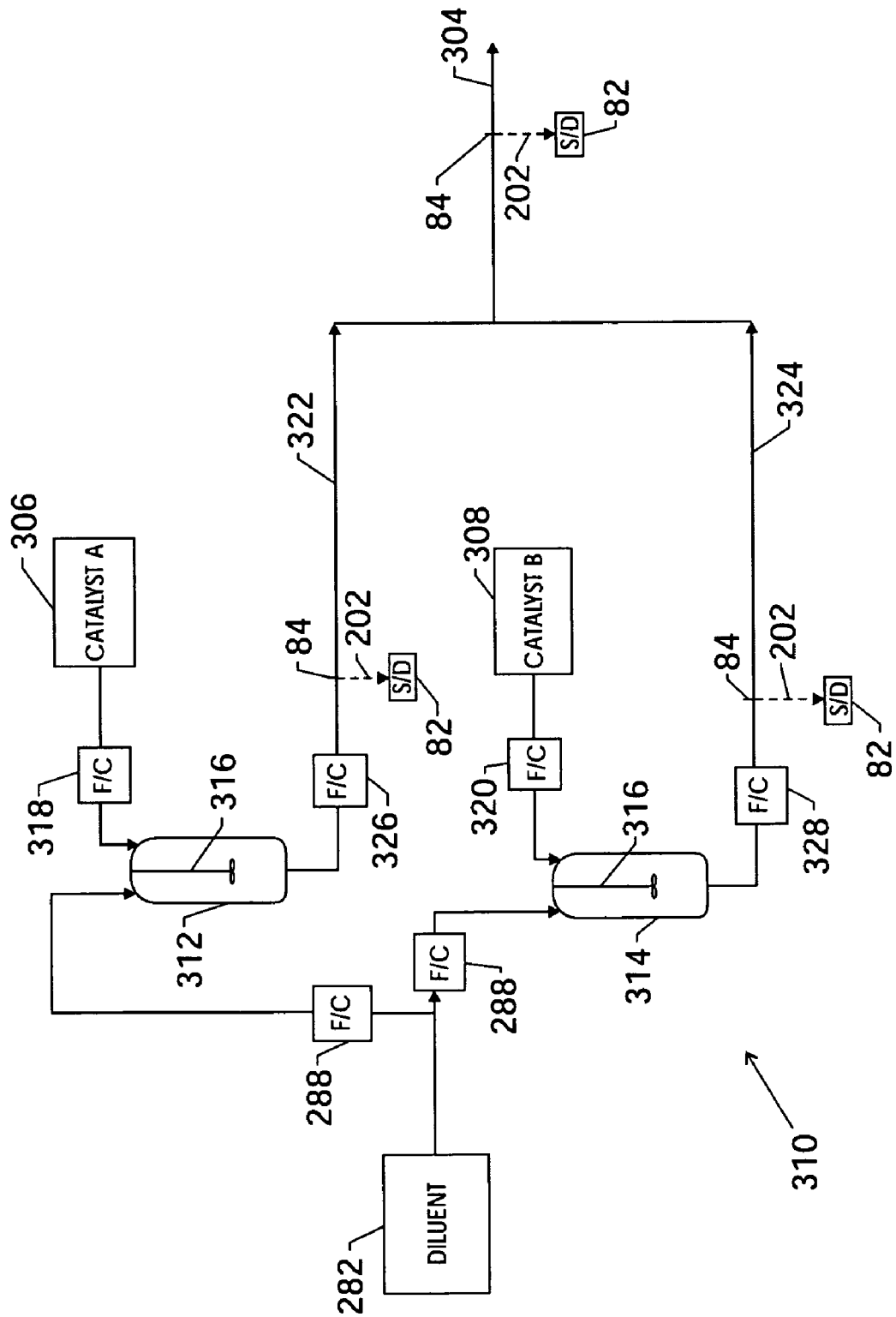
FIG. 23 depicts a catalyst feed system in accordance with one embodiment of the present techniques.

One or more of the catalysts 306 and 308 may be monitored via Raman spectrometry via the techniques discussed herein. In particular, one or more Raman probes may be situated in the catalyst feed system 310, the respective catalyst feed stream 304 or streams, and/or the reactor subsystem 20. For example, a Raman probe 84 may be situated in process piping downstream of the respective catalyst mix tanks 312 and 314, either before or after the catalyst slurries have been combined, as depicted in FIG. 23. The respective probes 84 may acquire Raman spectral data 202, which can be used to determine catalyst concentrations, catalyst flow rates, and the ratio of catalysts to one another. These various factors may be of interest to maintain the rate of polymerization within the reactor subsystem 20, the desired polymer properties, and/or the stability of the reactor subsystem 20.

In response to the catalyst measurements determined from the Raman spectral data 202, one or more adjustments 264 may be made to obtain the desired concentration of a catalyst 306 or 308 or the desired ratio of catalysts 306 and 308. For example, one or more valves or flow controllers 288, 318, or 320 may be adjusted to alter the flow rate of diluent 282 or catalyst 306 or 308 into a mix tank 312 or 314, the agitation rate within a mix tank 312 or 314 may be adjusted, the flow rate of catalyst slurry out of a mix tank may be adjusted, or the flow rate of one or more catalyst feed streams 322 or 324 into a catalyst feed stream 304 or into the reactor subsystem 20 may be adjusted, such as by a flow controller 326 or 328 or valve arrangement.

Additionally, as will be appreciated by those skilled in the art, catalyst feed systems 310 may include additional processing steps, such as the use of contact pots, prepolymerizers, and other catalyst preparation vessels. The operating conditions, such as temperature and/or agitation, of these additional processing steps may also be adjusted in response to the Raman spectral data 202 or the determination of a catalyst concentration or ratio. Adjustments to these additional steps may also be affected by the control techniques discussed herein and may include changing the set point on a thermostat or adjusting an agitation rate.

C. Reactor Subsystems

The various possible feed streams 18, 27, 296, and 304 processed by the reactor feed subsystem 16, discussed above, supply a reactor subsystem 20 with reactants, catalysts 306 and 308, and so forth. The reactor subsystem 20 itself may comprise one or more polymerization reactors, which may in turn be of the same or different types. Furthermore, in multiple reactor subsystems, the reactors may be arranged serially or in parallel. Whatever the reactor types comprising the reactor subsystem 20, a polyolefin particulate product, generically referred to as "fluff" herein, is produced. To facilitate explanation, the following examples are limited in scope to specific reactor types believed to be familiar to those skilled in the art and to single reactors or simple combinations. To one skilled in the art, however, the present techniques are simply and easily applicable to more complex reactor arrangements, such as those involving additional reactors, different reactor types, and/or alternative ordering of the reactors or reactor types. Such arrangements are considered to be well within the scope of the present invention.

1. Liquid Phase

For example, one reactor type comprises reactors within which polymerization occurs within a liquid phase. Examples of such liquid phase reactors include stirred tank reactors, loop slurry reactors 340, autoclaves, tubular reactors, and also boiling liquid-pool reactors. For simplicity, loop slurry reactors 340 will be discussed in the context of the present techniques though it is to be understood that the present techniques are similarly applicable to other types of liquid phase reactors.

Figure 24:
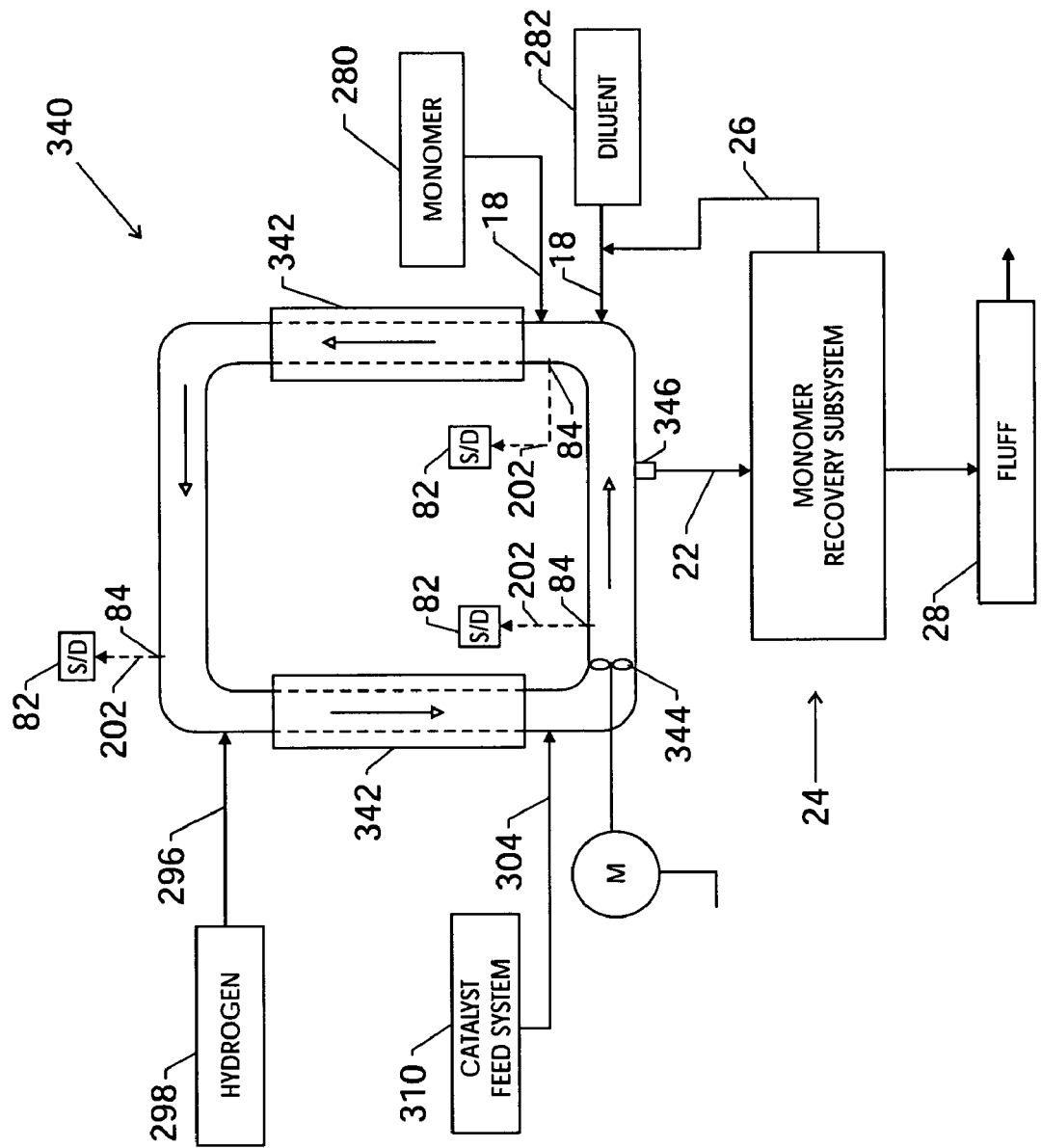
FIG. 24 depicts an exemplary loop slurry reactor in accordance with one embodiment of the present techniques.

Loop slurry reactors 340, as depicted in FIG. 24, are generally composed of segments of pipe connected by smooth bends or elbows such that a continuous flow path is provided that is substantially free from internal obstructions. A loop slurry reactor 340, for example, may be used to carry out PE or PP polymerization under slurry conditions in which insoluble particles of PE or PP are formed in a fluid medium and are suspended as slurry until removed. The fluid medium may include diluent 282, monomer 280, comonomer 284, additives, as well as any other desired coreactants, which are added to the reactor interior via inlets or conduits. Catalyst and hydrogen feed streams 304 and 296 may also be present. A cocatalyst may also be present, including catalyst activators, such as triethylaluminum alkyl, neat or diluted (e.g., in hexane). Similarly, one or more "donor" agents may be present, such as a silane, which may be used to control the stereospecificity, and thereby the crystallinity, of the polymerized polyolefin molecules.

The reaction conditions, such as temperature, pressure, and reactant concentrations, are regulated to facilitate the desired degree of polymerization and the desired reaction speed. Temperature, however, is typically maintained below that level at which the polymer product would go into solution. Due to the exothermic nature of the polymerization reaction, cooling jackets 342, through which a cooling fluid is circulated as needed to remove excess heat, may be provided around portions of the loop slurry reactor 340, thereby maintaining the temperature within the desired range, generally between 150° F. to 250° F. (65° C. to 121° C.). Likewise pressure may be regulated within a desired pressure range,- generally 100 to 800 psig, with a range of 450-700 psig being typical.

Raman probes 84 may be inserted at various points within the loop slurry reactor 340. For example, Raman probes 84 may be inserted, using an insertion/retraction mechanism 180 such as that depicted in FIG. 10, within the reaction loop, such as near the inlet of a feed stream, near an impeller 344 to sample the turbulent slurry mixture, and/or within a continuous takeoff point or settling leg 346 to sample the clear liquid above the polyolefin fluff 28. Due to the exposure of the probe 84 to adherent particulates, i.e., the polymerizing polyolefin, the probe 84 may be fitted with a ball 122 or mushroom type lens 154, such as a sapphire ball lens, to prevent particle adhesion, as discussed above. A 785 nm Raman system may be used to obtain the measurements. In one embodiment, the scattered Raman signal may be collected for some period, such as 240 seconds, prior to integration into a spectrum for analysis The Raman spectral data 202 obtained from within the reactor 340 may be used to determine chemical concentrations and/or the ratios of reactants or catalysts 306 and 308, as discussed with regard to the reactor feed subsystem 16. In addition, the Raman spectral data 202 obtained from within the reactor 340 may be used to make other determinations as well. For example, the obtained Raman spectral data 202 may be used to determine the physical, mechanical, rheological, and/or melt properties, such as density, MFR, MI, crystallinity (such as via the measurement of xylene insolubles) and/or copolymer content, of the polyolefin fluff 28. Similarly, the Raman spectral data 202 may be used to determine the percent solids, typically 30%-70% by weight, within the reactor 340. In particular, determination of percent solids may be used to measure the differential settling gain in different parts of the loop, such as in a continuous takeoff outlet relative to other portions of the loop. Because spectral data 202 may be obtained in a substantially real time manner, it may also be possible to determine and track the reaction rate based upon the known flows into and out of the reactor 340 along with the measurement of percent solids or other polyolefin measures.

In response to these various possible measurements, the production process may be adjusted. For example, based upon the measurements of concentrations or the determined ratios, percent solids or polyolefin properties the flow rates of one or more feed streams 18, 26, 296, or 304 may be adjusted, such as by a valve, flow controller, compressor, or displacement pump. In this manner, the concentration of reactants, diluent 282, catalyst 306 and 308, and/or hydrogen 298 may be adjusted based upon the monitored data, i.e., the Raman spectral data 202, to maintain reactor stability and/or the uniformity of the properties of the polyolefin fluff 28. Similarly, adjustments may be made to the temperature or pressure within the reactor 340, such as via changing the set point on a thermostat or temperature gauge or the flow rate of coolant through the cooling jackets 342. In particular, the temperature and/or pressure may be adjusted in response to a calculated reaction rate which deviates from the desired rate. In this manner, a consistent polymer fluff 28 possessing the desired properties may be produced by the liquid phase reactor 340.

2. Gas Phase

Figure 25:
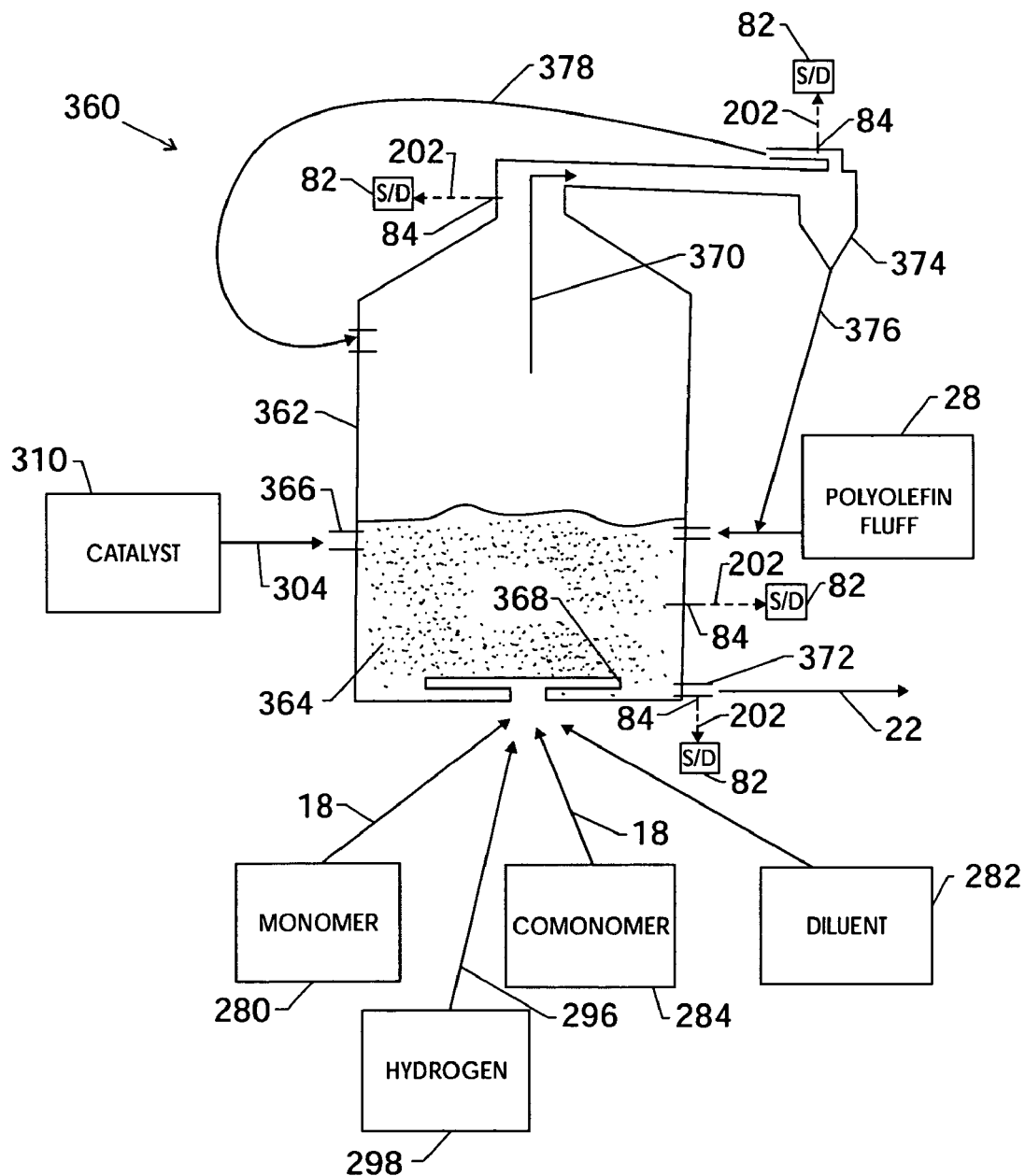
FIG. 25 depicts an exemplary gas phase reactor in accordance with one embodiment of the present techniques.

The present techniques may be also be used with a gas phase polyolefin reactor 360, as depicted in FIG. 25. Gas phase reactors 360 typically operate as horizontally-stirred bed, vertically-stirred bed, or as a fluidized bed, and at lower pressures than liquid phase reactors. Gas phase reactors 360 typically comprise reactor chambers 362 containing catalyst 306 and 308 which may become fluidized within a bed of particles 364. Additional catalyst 306 and 308 may be added to the bed, such as via a catalyst inlet 366. The gaseous feed streams 18 and 296 enter the reactor 360, typically from a distributor 368 on the bottom of the reactor 360, such as near the plug flow, and pass through the bed to form polyolefin product. In addition, the recovered components stream 26 may enter the reactor 360 in a gaseous form or in a gaseous and liquid form, depending on the degree of condensation in the recovered components stream 26. The feed streams may include monomer 280, comonomer 284, diluent 282, and hydrogen 298. An additive feed stream, such as a stream of anti-fouling agent may also be present. Additionally, if the reactor 360 is part of a chain of reactors a stream of polyolefin fluff 28 containing active levels of residual catalyst 306 and 308 may also be introduced to the reactor 360.

Unreacted gases exit the reactor from the top as an overhead gas stream 370 while the polyolefin fluff 28 exits the reactor 360 from a discharge 372 at or near the bottom of the reactor 360. The overhead gas stream 370 may enter a cyclone 374 where fine polyolefin particulates or "fines" and any catalyst particles are separated from the overhead gas stream 370 and recycled to the reactor 360 as a fines stream 376. A cyclone overhead gas stream 378 also exits the cyclone 374 and may contain monomer 280, comonomer 284, hydrogen 298 and/or diluent 282. The cyclone overhead gas stream 378 may be recycled to the reactor 360 or to a recovery system or may be flared.

Gas phase reaction generally provides greater specificity in polyolefin copolymer production than liquid phase reactions, allowing the production of specified co-polymers as opposed to polymers in which the respective monomers are randomly distributed. For example, gas phase reactors 360 typically facilitate production of block or heterophasic copolymers. Additionally, because of the relatively low mass of monomer 280 and comonomer 284 present in gas phase reactors 360 compared with that in liquid phase reactors, the discharge stream produced by the gas phase reactor 360 may be less demanding of a downstream monomer recovery operation.

A Raman probe 84 may be situated in the overhead gas stream 370 and/or the cyclone overhead gas stream 378 to measure chemical concentrations, such as reactant concentrations and/or ratios. Similarly, a Raman probe 84 may be situated in the fluidized bed region or the plug flow region to measure chemical concentrations and/or to determine product properties such as density, MFR, comonomer content, and so forth. A Raman probe 84 may also be situated at the discharge 372 of the reactor 360 to determine the properties of the polyolefin fluff 28 at this location. For example, in one implementation, PE copolymer polymerization may occur within a reactor 360 in a range from 250 p.s.i.g to 350 p.s.i.g. A 785 nm low resolution Raman system may acquire spectral data 202, such as via a probe 84 in the overhead gas stream 370, which may be used to determine the presence and concentration of ethylene and hexene in the reactor 360. Similarly, a 532 nm laser system may be used to obtain the Raman spectral data 202 useful for detecting and measuring hydrogen 298.

In response to these measurements and/or determinations, adjustments 264 may be made to the flow rates of monomer 280, diluent 282, comonomer 284, hydrogen 298 and/or recycled polymer 384 to obtain the desired concentrations within the reactor 360 and/or to produce polyolefin with the desired properties. In addition, the pressure, temperature, bed level, catalyst feed rate, additive feed rate, and so forth, within the reactor 360 may be adjusted in response to the Raman spectral data 202 or to properties determined from the spectral data 202, such as monomer/comonomer conversion rates in the reactor 360 or comonomer 284 content in the polyolefin fluff 28. The determination of polyolefin properties may be made using the chemometric techniques discussed herein.

3. Reactor Trains and Combined Phases

Figure 26:
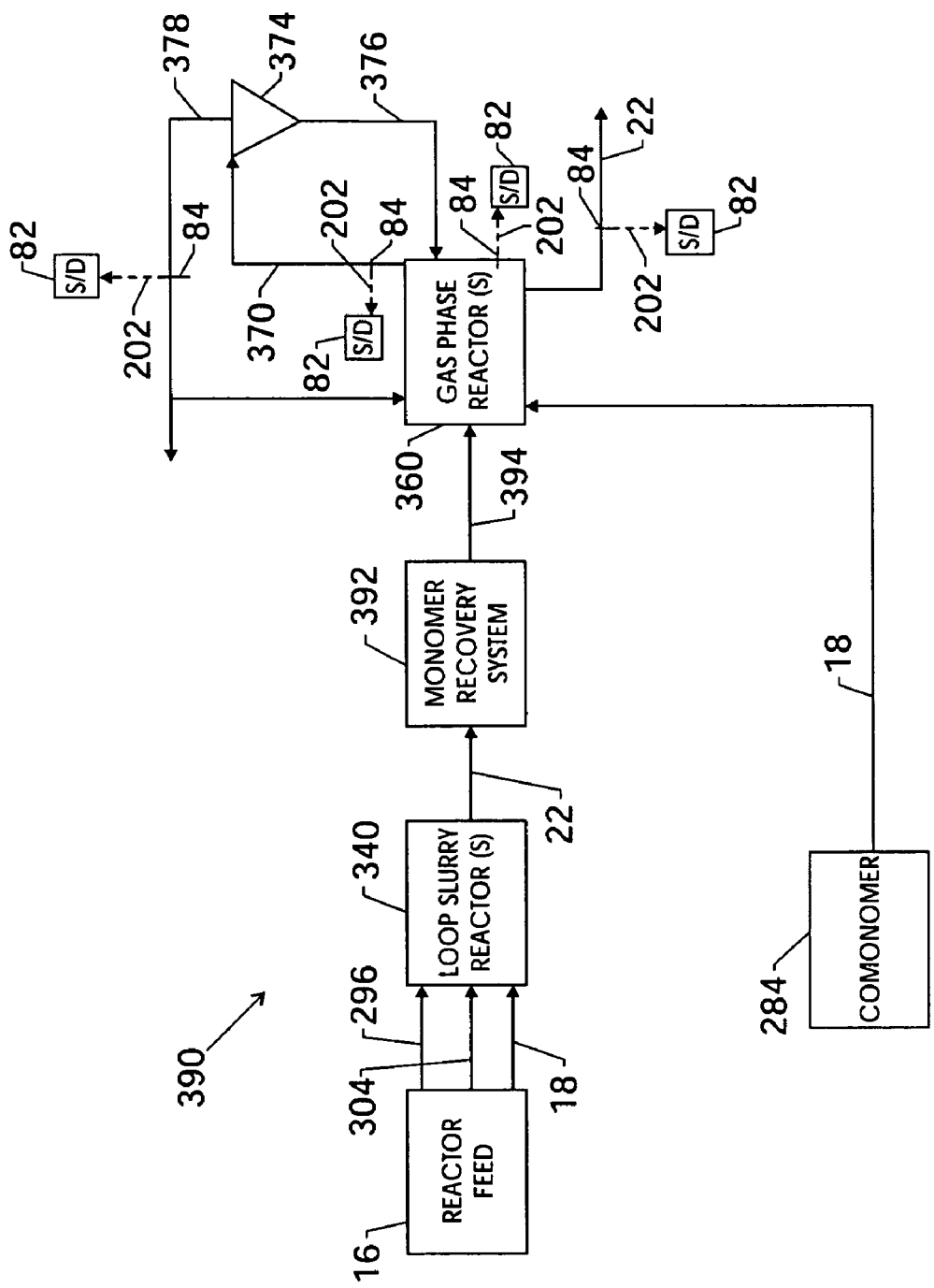
FIG. 26 depicts a reactor train and recovery system in accordance with one embodiment of the present techniques.

As noted above, the reactor subsystem 20 may comprise more than one reactor, including combinations of liquid and gas phase reactors. Indeed, various reactors and reactor types may be sequentially "trained" together to obtain the desired polyolefin fluff product 28. For example, referring now to FIG. 26, a block diagram depicts an exemplary polyolefin reactor train 390. The depicted reactor train 390 of the reactor subsystem 20 includes one or more loop slurry reactors 340 with associated slurry discharges 22, an intervening monomer recovery system 392, and one or more gas phase reactors 360. As one skilled in the art will readily apprehend, the reactor train 390 may instead comprise only loop slurry reactors 340, only gas phase reactors 360, or an alternative order or sequence of loop slurry reactors 340 and gas phase reactors 360. In an alternative embodiment, the loop slurry reactors 340 may instead comprise one or more boiling liquid-pool reactors.

The intervening monomer/diluent recovery subsystem 392 processes the slurry discharge 22 through one or more flash vessels to produce a processed discharge 394. The processed discharge 394 will typically have residual active catalyst 306 and 308 with the processed polyolefin. A gas phase reactor 360 may receive the processed discharge 394 as a feed stream. In addition, the gas phase reactor 360 may receive a comonomer 284 feed stream 18 independent of any comonomer feed received by the loop slurry reactors 340. A gas phase reactor overhead system, as depicted in FIG. 25, may also be present. The polyolefin fluff 28 that exits the gas phase reactor 360 may be processed by a downstream monomer recovery subsystem 24, by a second gas phase reactor 360, or by other downstream processes. Though the present embodiment is depicted as incorporating an intervening monomer recovery subsystem 392, the intervening recovery subsystem 392 may be absent.

As discussed with regard to FIG. 25, Raman probes 84 may measure monomer 280, comonomer 284, and/or diluent 282 concentrations in the overhead gas streams 370 and 378 of the one or more gas phase reactors 360. Similarly, polyolefin properties, such as density, MFR and/or comonomer content may be measured in the gas phase reactor 360, such as in the bed, and/or in the discharge piping.

In such a train 390, monitoring may occur as discussed with regard to FIGS. 24 and 25 with the additional possibility of monitoring in the intervening monomer recovery system 392, as will be discussed below with regard to monomer recovery system 24. In addition, adjustments and control may generally proceed as discussed with regard to FIGS. 24 and 25 with the additional possibility of adjustments to upstream reactors and processes. For example, chemical concentration measurements or polyolefin property determinations made from Raman spectral data 202 obtained from the gas phase reactor 360 may prompt upstream adjustments. Such upstream adjustments may include adjusting the feed rate of the reactor feed streams 18, 26, 296, or 304 to the loop slurry reactor 340, such as by adjusting a valve, flow controller, compressor, or displacement pump. Similarly, gas phase measurements and/or determinations may prompt adjustment of the loop slurry reactor conditions, such as to temperature, pressure, or agitation. In particular, the desirability of upstream adjustments increases as the residence time between the respective processes decreases. In addition, as will be discussed in greater detail below, adjustments may be made to the intervening monomer recovery system 392, such as by adjusting the temperature or pressure of the recovery system 392, based upon measurements or determinations made from Raman spectral data 202 obtained downstream.

D. Fluff and Reactant Separation and Recovery

After polymerization of the polyolefin fluff 28 within the reactor subsystem 22, the fluff discharge 22, containing the polyolefin fluff 28 and any residual non-polyolefin contaminants may be separated or, in the case of catalyst 306 and 308, deactivated. Typically this process is referred to, somewhat narrowly, as monomer recovery. In general, a monomer recovery subsystem 24 may comprise a series of discrete columns, such as purge columns 400, and/or degas vessels, such as high and low pressure flash vessels 402 and 404. The columns 400 or vessels 402 and 404 may operate in a plug flow or fluidized manner.

Figure 27:
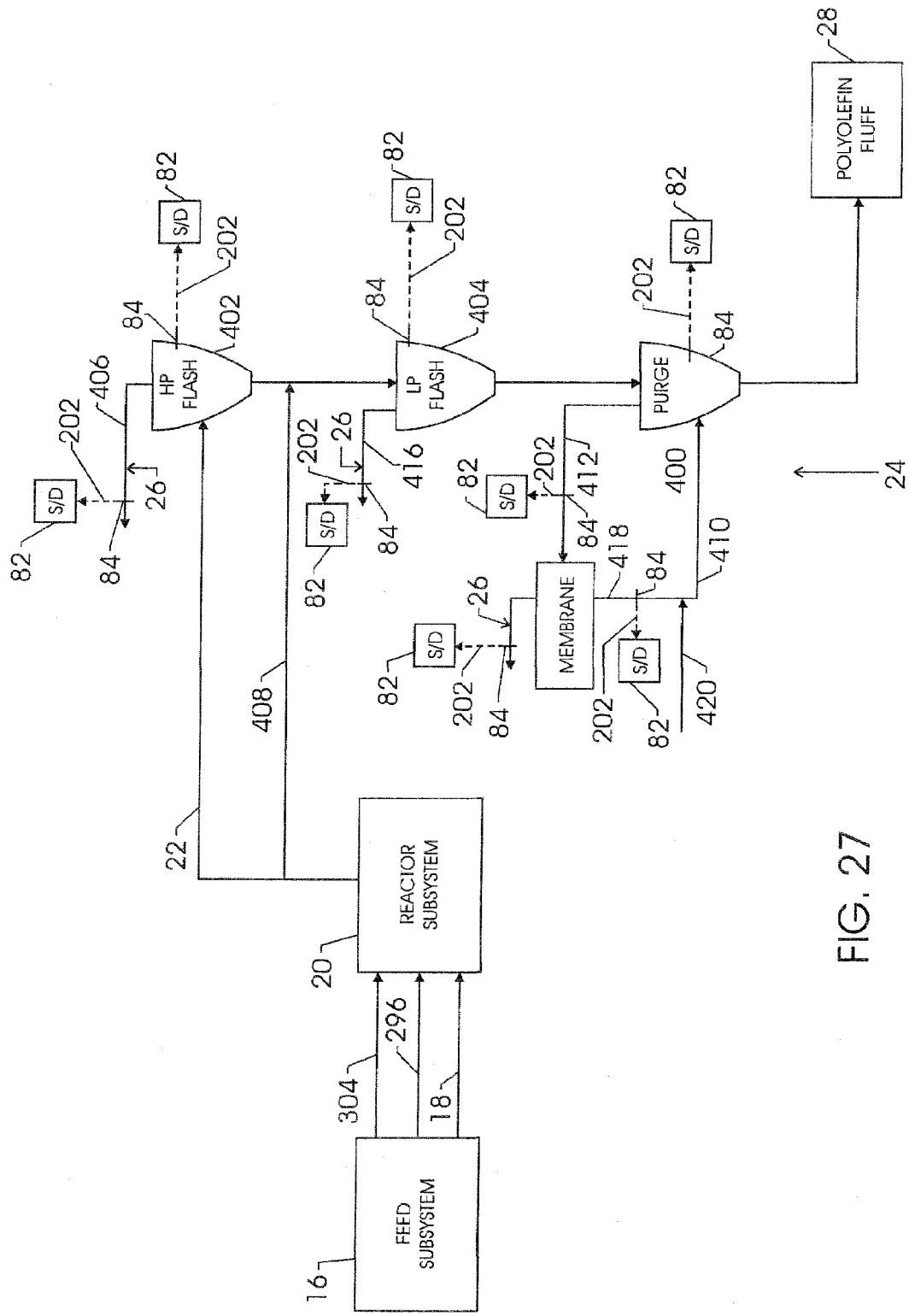
FIG. 27 depicts a liquid phase reactor system, reactor feed system, and recovery system in accordance with one embodiment of the present techniques.

Referring now to FIG. 27, a block diagram depicts the monomer recovery process of an exemplary polyolefin production process. The reactor subsystem 20 produces a fluff containing discharge 22, as discussed above, which contains residual reactants and/or diluent 282 to be recovered. The discharge 22 may also contain catalyst which, if polymerization is completed, may be deactivated by the addition of a catalyst poison, such as carbon monoxide, carbon dioxide, steam, and so forth. The discharge 22 from the reactor subsystem 20 may first enter a high pressure flash vessel 402 where the reactants, diluent 282, and so forth are exposed to sufficient temperature to evaporate many of the non-polyolefin components, which may be removed as and recovered in an overhead gas stream 406. The recovered components 26 may subsequently be used in future polymerization reactions.

The discharge 22 may be further processed in a low pressure flash vessel 404 to recover additional non-polyolefin components 26 from the low pressure flash vessel overhead gas stream 416. Alternately, the discharge 22 may be returned to the reactor subsystem 20 for additional reaction in a different reactor. In such cases, the return polyolefin discharge 408 may enter the monomer recovery subsystem 24 at the low pressure flash vessel 404 as opposed to the high pressure flash vessel 402. After treatment through the low pressure flash vessel 404, the discharge 22 may be processed by a purge column 400. In some cases the purge column 400 may utilize a nitrogen gas stream 410 to strip residual monomer 280, comonomer 284, and/or diluent 282 from the fluff 28. The purge column overhead gas stream 412 may then be recycled through a reverse osmosis membrane unit 414 to refresh the nitrogen stream 410 for return to the purge column 400. The recovered residual components 26, such as monomer 280 and diluent 282, may be flared or recycled. A purified polyolefin fluff 28 typically results from the passage of the discharge 22 through the monomer recovery subsystem 24.

Raman probes 84 may be situated to obtain spectral data 202 at various points in the monomer recovery process. For example, Raman probes 84 may be situated in the vessels 402 and 404, the columns 400, or the interconnecting conduits between the respective vessels 402 and 404 and columns 400. Spectral data 202 obtained in the conduits may be used to measure chemical concentrations to determine the quantity of non-polyolefin components remaining in the discharge 22 as monomer recovery progresses. In addition, the spectral data 202 obtained in the conduits may be used to determine one or more of the various physical, mechanical, rheological, or melt properties of the polyolefin fluff 28. Raman probes 84 may also be situated in the respective overhead gas streams 406, 412, and 416 associated with the vessels 402 and 404 and columns 400. Spectral data 202 obtained in the overhead gas streams 406, 412, and 416 may be used to measure the chemical concentrations of the recovered components 26, i.e., diluent 282, monomer 280, comonomer 284, and so forth, which may be used to determine the efficiency of the recovery process and/or to properly meter the recovered components 26 back into the reactor subsystem 20. Similarly, a Raman probe 84 may be situated downstream of the membrane filter 414 associated with the purge column 400 to obtain spectral data 202 of the filtered nitrogen gas 418 being returned to the purge column 400. Spectral data 202 obtained downstream of the membrane 414 may be used to measure the chemical concentration of recovered components 26 in the purge gas 412 and thereby to determine the relative purity of the purge gas 412.

Different locations of the Raman probes 84 within the monomer recovery subsystem 24 may offer different advantages. For example, the upstream positions may provide monitor data with less residence time, i.e., less time between the measured point and the control point. Downstream locations, by contrast, may offer operability and maintenance advantages because the polyolefin fluff 28 is being monitored at lower pressure and with less residual monomer 280.

Adjustments may be made to the production process based upon the measured chemical concentration or the determined fluff properties, as determined from the respective Raman spectral data 202. For example, the flow rate of one or more recovered reactants or of diluent 282 into the reactor subsystem 20 may be adjusted in response to the measured concentrations of reactants or diluent 282 in the recovered components 26 or in response to the determined properties of the polyolefin. Similarly, catalyst addition rate or reactor conditions may be adjusted based upon the concentration of various reactants in the recovered component gas streams 406, 412, and 416 or upon the determined properties of the polyolefin. Because of the rapid turnaround of the Raman spectrometry system, fluff properties, such as density, MFR, and/or MI, may be determined within five minutes instead of hours, as may be incurred with laboratory analysis. As a result, adjustments may be made at the reactor level such that off spec fluff product or variability in the fluff product is minimized.

In addition, the operating conditions, such as flow rate, temperature, and/or pressure, of the flash chambers 402 and 404 and/or the purge column 400 may be adjusted to improve recovery efficiency in response to the measured downstream concentration of reactants. Similarly, the operating conditions of the filter 414 processing the purge column overhead gas stream 412 or the addition rate of fresh nitrogen gas 420 to the purge column 400 may be altered based upon the reactant and diluent concentrations measured downstream of the filter 414.

While the depicted embodiment is one possible configuration of a monomer recovery subsystem 24, various configurations for treating the polyolefin discharge 22 from the reactor subsystem 20 exist other than that described herein. One skilled in the art will understand how the present principles may be applied to different configurations of a monomer recovery subsystem 24.

E. Extruder Feed Subsystems

After processing by the monomer recovery subsystem 24, the purified fluff 28 may, in some circumstances, be transported to a customer site for further processing. Typically, however, the purified fluff 28 is further processed to form polyolefin pellets 36 prior to shipment to a customer 30. In particular, the purified fluff 28 may be fed to an extruder/pelletizer 40 which subjects the purified fluff 28 to heat and/or pressure, extruding polyolefin pellets 36 which may then be shipped.

1. Fluff Blending

Prior to extrusion and pelletization, the various batches of purified fluff 28 may be combined and blended to form an extruder feed stream 34. For example, two batches of purified polyolefin fluff 28 with differing properties may be blended to produce polyolefin pellets 36 with properties between those of the two batches of fluff 28. For example, polyolefin pellets 36 with desired density, comonomer content, modulus, crystallinity, and/or melt properties may be produced by blending two batches of fluff 28 with properties bracketing the desired properties. Alternately, small amounts of purified fluff 28 which do not possess the desired properties may be blended with a large amount of conforming fluff 28 to produce conforming pellets 36.

Figure 28:
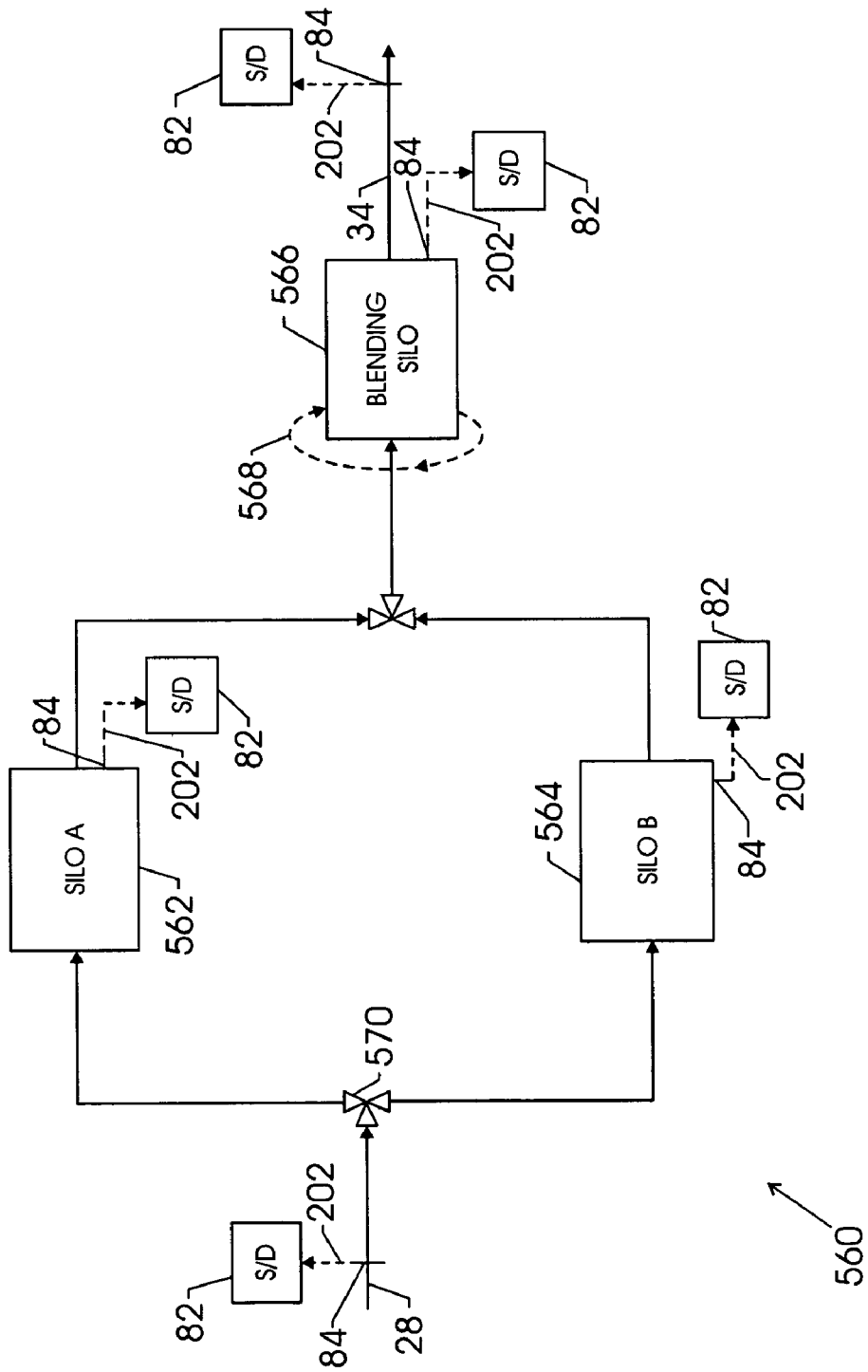
FIG. 28 depicts a post-reaction sorting and blending system in accordance with one embodiment of the present techniques.

An example of such a blending system 560 is depicted in FIG. 28. In the exemplary system, incoming purified fluff 28 is sorted, based on its properties, to different storage silos 562 and 564, two of which are shown. Based on the desired properties of the pellets 36, fluff 28 from the different silos 562 and 564 may be metered into a blending silo 566 in proportions that will produce the desired properties upon extrusion and pelletization. The fluff 28 may be blended in the blending silo 566 by means of a recirculating system 568 or mechanical agitator. The blended fluff may then be fed to the extruder/pelletizer 40 as an extruder feed 34.

Raman probes 84 may be located at various points within the blending process. Alternately, sample points may be located at various points within the process whereby an operator 58 may remove a fluff sample for testing using a handheld Raman device 100, as discussed herein. For example, referring to FIG. 28, a Raman probe 84 may be situated, or a sample taken, prior to sorting of the fluff 28 into the respective storage silo 562 and 564. Similarly, Raman probes 84 may be situated, or samples taken from, the respective storages and blending silos 562, 564, and 566 or from the discharged fluff blend. Spectral data 202 of the blended fluff comprising the feed stream 34 may be integrated over an interval, such as 240 seconds, such that the spectral data 202 accurately represent the composition of the blend. The Raman spectral data 202 obtained at these sample points may be used to derive properties, such as density, comonomer content, and/or melt properties, of the polyolefin fluff 28 or the blended extruder feed 34.

The determined properties may then be used to adjust the sorting and blending process. For example, fluff properties determined prior to sorting may be used to sort the fluff 28 into the proper storage silo 562 and 564, such as by adjusting a three-way valve 570 to direct flow into particular storage silos 562 and 564. Fluff properties determined prior to blending may be used to confirm that the fluff 28 selected for blending has the desired properties and that it is added at the proper rate or in the right amount to produce the desired blend. Similarly, the properties of the fluff blend in the blending silo 566 or the extruder feed 34 may be used to adjust the blending process, such as by changing the addition rate of fluff 28 from a storage silo 562 and 564. The properties of the blended fluff may also be used to determine the properties of the extrusion process-or whether the blend is out of spec.

2. Additives

Figure 29:
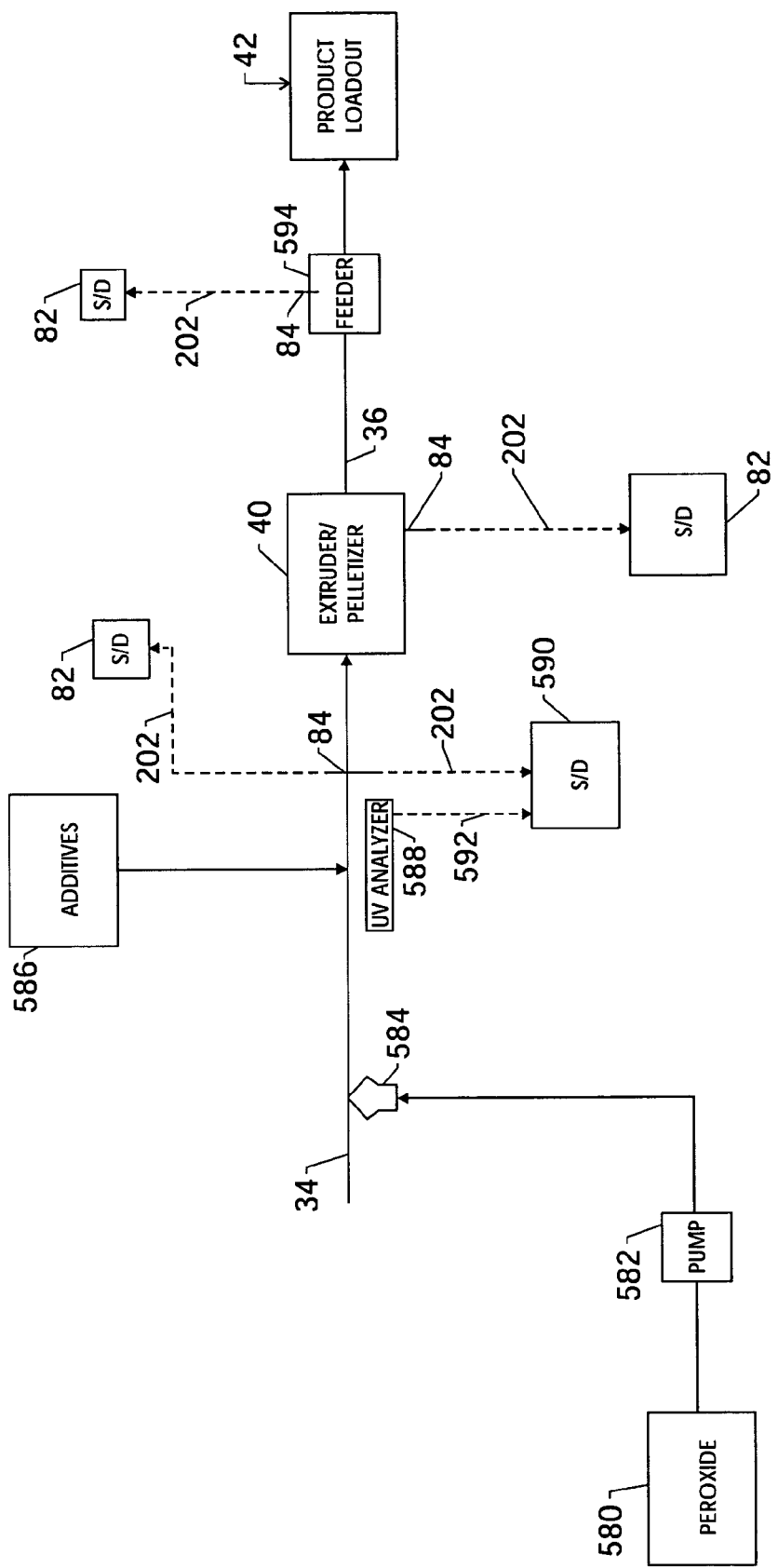
FIG. 29 depicts a post-reaction extrusion system in accordance with one embodiment of the present techniques.

In addition to purified fluff 28, whether blended or not, the extruder feed 34 may also comprise one or more additives to alter the polyolefin properties or to add new properties to the resulting polyolefin. Referring to FIG. 29, ultraviolet light (UV) inhibitors, impact modifiers, blowing agents, peroxides, and the like, may be added to the extruder feed 34 to enhance the properties of the polyolefin. The extruder feed 34 with the additives may then be extruded and pelletized to form polyolefin pellets 36 with the desired properties.

Peroxides 580 may be added to control the viscosity of the extruder melt. For example, in PP extrusion, peroxide 580 may break some of the long polymer chains, thereby lowering the viscosity of the melt and increasing the melt flow rate. In contrast, in PE extrusion, peroxide 580 may promote cross-linking of the polymer chains, increasing the viscosity of the melt and decreasing the melt index. The peroxide 580 may be added to the extruder feed 34 by a pump 582 that sprays the peroxide 580 onto the extruder feed 34 via a nozzle 584.

In addition, a UV inhibitor may be added to the extruder feed as a powdered additive 586. The UV inhibitor may absorb or reflect UV light in a polyolefin product, thereby preventing breakage of the polyolefin chains. In this way, the UV inhibitor may protect the polyolefin comprising whatever final product is formed from the polyolefin. In addition, other additives 586 may be added to the feed stream 34, such as tints or dyes, to make the polyolefin more acceptable for its intended purpose.

Raman probes 84 may be situated to monitor the extruder feed 34, such as after the addition of peroxide 580, UV inhibitors, and/or other additives 586. The spectral data 202 acquired by the probe 84 may be used to measure the chemical concentration of the peroxide 580 and/or other additives 586 and/or to determine the feed properties, such as density, comonomer content, melt flow rate, and/or melt index. Adjustments may be made to the respective addition rates based upon the measured chemical concentrations. In this manner, the desired amount of peroxide 580 and/or additive 586 may be added to achieve the desired polyolefin property or properties, including melt properties, color, and UV protection, after extrusion.

In addition, a UV analyzer 588 may be combined with Raman spectrometry for monitoring the extruder feed 34 after application of the UV inhibitor. For example, a dual channel detector 590 having an analog-to-digital board may be provided to simultaneously measure Raman spectral signals 202 on one channel and ultraviolet spectral signals 592 on the second channel. The Raman spectral data 202 may be used to determine fluff properties, such as density, comonomer content, and/or melt properties. The UV signal 592 may be used to monitor additives, such as UV inhibitors, tints, and/or dyes. The resulting simultaneous signals may be processed and displayed by a computer, such as a workstation in a distributed control center.

F. Extrusion

Once the extruder feed 34 is formed, by fluff blending and/or the addition of additives 586 and/or peroxide 580, the feed 34 may be provided to an extruder/pelletizer 40 as a polyolefin melt. The melt is subjected to heat and/or pressure and extruded through a pelletizer as polyolefin pellets 36. Once cooled, the pellets 36 may be sorted and loaded in a transport vessel for shipment to a customer 30.

A Raman probe 84 may be situated in the extruder 40 above the melt, such as in the barrel of the extruder, to obtain spectral data 202 of the melt. In addition, a Raman probe 84 may be situated after the extruder/pelletizer 40 to obtain spectral data 202 of the polyolefin pellets 36. For example, a Raman probe 84 may be situated in a flow of pellets 36 in a vibrating feeder 594. The probe 84 may be situated so that it is not in contact with the pellets 36, such as 2 to 10 mm above the sample.

Figure 30:
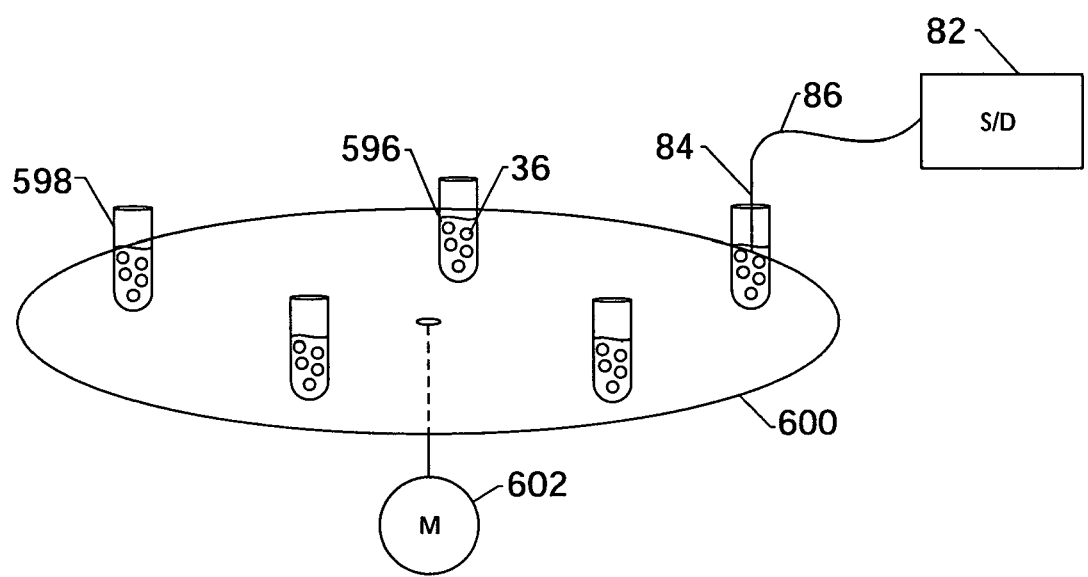
FIG. 30 depicts a rotating sample holder in accordance with one embodiment of the present techniques.

Alternately, the pellets 36 may be sampled and Raman spectral data 202 obtained off-line. In an off-line context, the pellets 36 may be sampled or they may be formed into a plaque which is sampled. For example, in one embodiment, the hot, typically between 140°-160°, freshly extruded pellets 36 may be cooled to room temperature in water, causing the polyolefin to crystallize. The pellets 36 and a measured amount of water 596 are placed in a vessel 598 mounted on a rotatable platform 600, as depicted in FIG. 30. The pellets 36 may be circulated in the water 596 and a Raman probe 84 inserted into the water 596. As the pellets 36 circulate within the water 596, the Raman probe 84 is focused on different pellets 36, allowing measurements to be made of the different pellets 36 and spectral data 202 to be integrated which adequately represents the sample. Based on the integrated spectrum, the density, or other properties, of the pellets 36 may be determined within one minute. The probe 84 may be withdrawn, the rotating stage 600 rotated, such as by a small electrical motor 602, and the probe 84 inserted into the next vessel 598 for sample measurement.

The Raman spectral data 202 of the melt and/or of the pellets 36 may be used to determine the polyolefin density, comonomer content, modulus, crystallinity, melt flow rate, melt index, or other physical, mechanical, rheological, and/or melt properties or to measure the chemical concentration of one or more additives 586 and/or peroxide 580. Alternatively, the distribution of polymer constituents and/or additives 586, such as blowing agents, impact modifiers, and so forth, may be determined from the Raman spectral data 202 of the pellets. Based upon the determined property or properties, various adjustments 264 may be made to the fluff production process and/or the pellet production process. For example, based upon the determined properties, a different extruder feed stream 34 may be diverted to the extruder/pelletizer 40 or the operating conditions of the extruder/pelletizer 40, such as temperature and/or pressure, may be adjusted. Similarly, the blend of fluff 28 comprising the extruder feed 34 may be adjusted, as discussed above, to produce pellets 36 with the desired physical, mechanical, rheological, and/or melt properties.

In regard to the additive 586 and/or peroxide 580 concentrations, an adjustment 264 may be made to the addition rate or rates or to the flow rate of the extruder feed 34. In this manner, a desired concentration or ratio per unit of feed 34 may be obtained. The additive 586 and/or peroxide 580 concentration may also be adjusted in response to the determined properties of the melt 34 and/or pellets 36. For example, the peroxide addition rate may be adjusted based upon the determined melt flow rate or melt index to obtain the desired melt flow rate or melt index. Similarly, the operating conditions, such as temperature and pressure, within the extruder/pelletizer 40 may be adjusted based upon the measured additive 586 and/or peroxide 580 concentrations.

In addition, adjustments 264 may be made further upstream based upon the polyolefin properties determined from the melt 34 or pellets 36. In particular, upstream adjustments may be especially useful in production schemes having reduced or minimal residence time between the reactor subsystem 20 and the extruder/pelletizer 40 such as when little or no inventory of polyolefin fluff 28 is maintained between the reactor subsystem 20 and the extruder/pelletizer 40. In such schemes, the polyolefin properties determined for the melt 34 or the pellets 36 may generate adjustments 264 to the flow rates of one or more reactant feed streams 18 or to the operating conditions of the reactor subsystem 20, such as temperature and pressure.

G. Storage and Load-Out

The polyolefin pellets 36 produced by the extrusion/pelletization process may be sorted and stored or loaded for shipment to customers 30. Though occasionally a customer 30 may wish to purchase the purified fluff 28 produced by the monomer recovery process, for simplicity the present discussion will be limited to load-out of pellets 36. However, one skilled in the art will understand how the present techniques, as they apply to pellets 36, may be adapted to apply to fluff 28.

1. Pellet Blending

Figure 31:
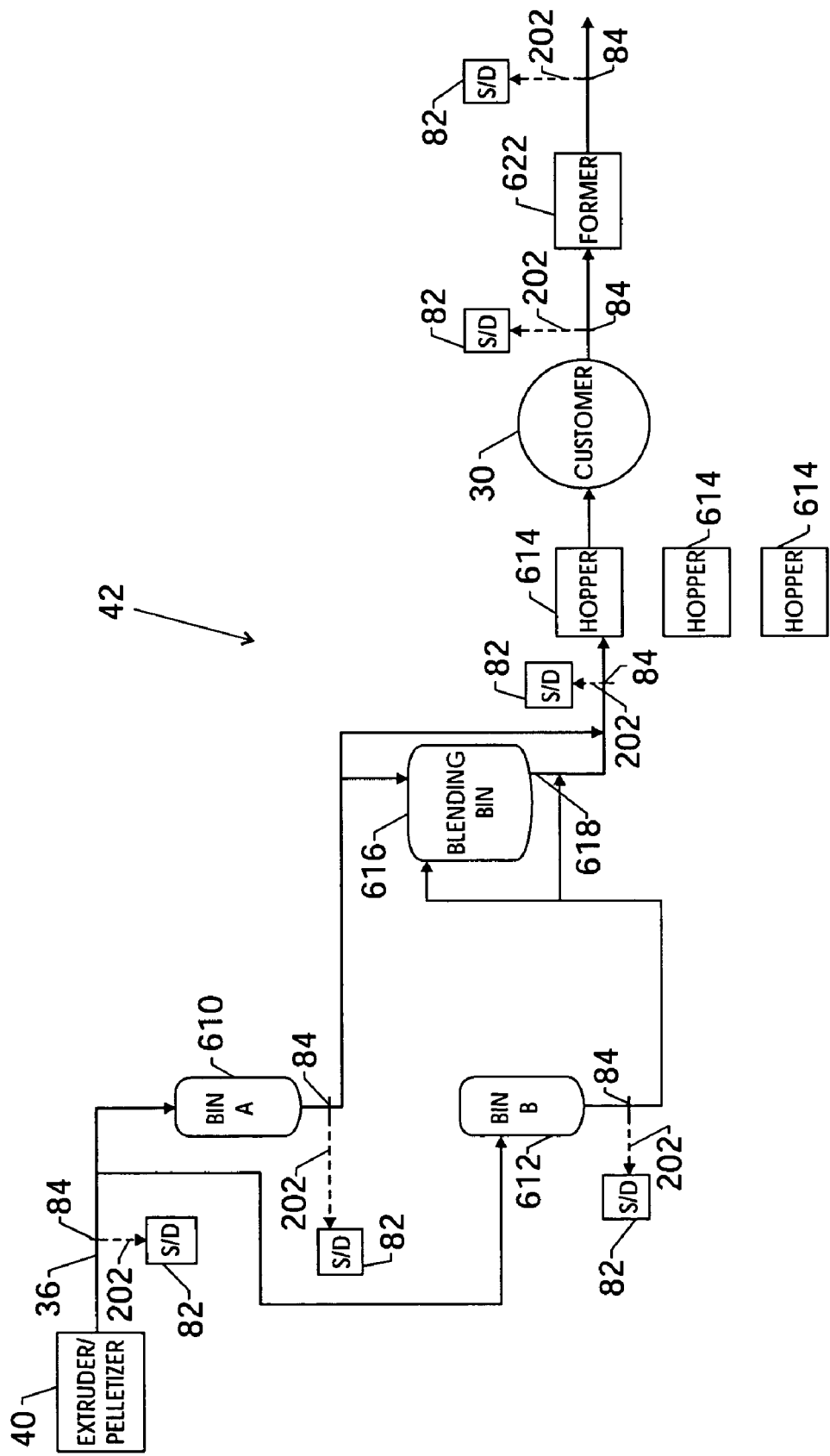
FIG. 31 depicts a post-extrusion sorting and blending system in accordance with one embodiment of the present techniques.

Typically a customer 30 may desire to purchase polyolefin pellets 36 having specific physical, mechanical, rheological, and/or melt properties, such as density, modulus, crystallinity, comonomer concentration, melt flow rate, and/or melt index. After pelletization, the pellets 36, if not immediately shipped, may be sorted and stored pending load-out and shipment. For example, referring to FIG. 31, pellets 36 having the same properties may be delivered to one or more storage bins 610 and 612. If the pellets 36 within a bin 610 or 612 meet the criteria specified by the customer 30, those pellets 36 may be selected during load-out and loaded, such as into hopper cars 614, for shipment to the customer 30. In some circumstances, such as where the pellets 36 are known to be within the customer's specifications, i.e., "in-spec", or where immediate shipment is desired, a bin 610 or 612 may be operated as a "wide" spot in the line, that is, maintained with little or no inventory level to provide minimal or reduced residence time.

However, if no pellets 36 in storage meet the customer's specification, a mixture of pellets 36 which, on aggregate, meet the specification may be blended from different storage bins 610 and 612. Likewise, small amounts of "off-spec" pellets 36 may be blended with "in-spec" pellets 36 to reduce or eliminate the off-spec inventory while still delivering an acceptable mixture of pellets 36 to the customer 30. If blending is desired, pellets 36 from different bins 610 and 612, and presumably with differing properties and/or additives, may be blended in pellet blending bin 616, such as by a recirculating loop or mechanical agitation. The ratio of pellets 36 from each storage bin 610 and 612 may be determined by the properties of the pellets 36 in each bin 610 and 612 and the properties desired of the pellet blend 618. In particular, the pellet blend 618 may be composed such that, on aggregate, the blend 618 is within the customer's specification, such as for density, MFR, modulus, crystallinity, additive concentrations, and so forth. The pellet blend 618 may be loaded out to a vehicle, such as a hopper car 614, for delivery to the customer 30.

One or more Raman probes 84 may be incorporated into the pellet storage and load-out process. For example, Raman probes 84 may be situated to obtain spectral data 202 of pellets 36 prior to sorting into the bins 610 and 612 and/or in the discharge of the storage and/or blending bins 610, 612, and 616. The spectral data 202 may be acquired over some interval, such as 120 seconds, such that the integrated spectrum accurately reflects a broad sample. The spectral data 202 obtained by the Raman probes 84 may be used to determine various properties of the pellets 36 or pellet blend 618, such as density, MFR, modulus, crystallinity, and so forth, or to determine the presence or distribution of one or more additives 586 or polymers in or on the pellets 36.

Based on the measured properties, the pellet sorting and blending process may be adjusted. For example, properties determined from spectral data 202 acquired between the extruder/pelletizer 40 and the storage bins 610 and 612 may facilitate the proper sorting of pellets 36 into the bins 610 and 612. Properties determined from spectral data 202 acquired between the storage bins 610 and 612 and the blending bin 616 may prompt a flow adjustment diverting or terminating the flow from a storage bin 610 or 612 if that bin 610 or 612 does not possess pellets 36 with the desired properties. If no blending process occurs, spectral data 202 acquired in the storage bin discharge may prompt the diversion or termination of the flow of off-spec pellets 36 to the load-out process. Similarly, spectral data 202 acquired in the blending bin discharge may prompt the diversion or termination of the flow of an off-spec pellet blend 618 to the load-out process.

2. Load-Out

Absent an indication that the product is off-spec, the sorted or blended pellets 36 or 618 may be loaded for transport to a customer site. The load-out process may comprise filling designated containers, such as railroad hopper cars 614, with the pellets 36 or blend 618 and preparing the containers or hoppers 614 for transit. Even if the proper pellets 36 are loaded, however, the hoppers 614 or containers may become disorganized during the process, particularly, if different types or grades of pellets 36 are being simultaneously prepared for shipment to one or more customers 30. Problems may arise, therefore, when in-spec pellets 36 are prepared for a customer 30 but are not properly routed during load-out due to poor tracking or communication procedures.

Raman spectrometry, particularly in the form of a handheld Raman spectroscope 100, may be used to improve tracking and to insure customer orders are properly filled. In particular, pellets 36 loaded into a hopper 614 or other vehicle may be sampled using a handheld Raman device 100. The Raman spectral data 202 thereby obtained may then be used to determine one or more Raman properties, such as density, comonomer content, modulus, crystallinity, melt flow rate, and/or melt index, which have been specified by the customer 30. In addition, the presence or distribution of one or more additives 586 on or in the pellets 36 may be determined from the spectral data 202. The determination of the property may be made locally, i.e., by the handheld Raman device 100, or remotely, i.e., by a computer or workstation 56 in wireless or radio communication with the device 100. Similarly, the Raman device 100 may update a centralized tracking database by wireless or radio means to allow centralized tracking of the load-out process.

Adjustments 264 may be made to the load-out process based upon the Raman spectral data 202. For example, hoppers 614 may be diverted to another customer 30 or emptied and refilled with different pellets 36 if they are found to contain off-spec pellets 36. Similarly, upstream blending or sorting may be adjusted based upon properties determined during load-out.

H. Customer Receipt and Processing

At the customer site, the pellet shipments are typically received, such as by hopper car 614, transferred to a storage site, such as a silo, and tested to determine if the polyolefin pellets 36 are in-spec. If the pellets 36 are in-spec, the customer 30 may process them by melting the pellets 36 and forming them into a polyolefin product 620. The polyolefin product 620 may be a final product, ready for retail, commercial, and/or industrial sale, or it may be a component to be incorporated into a final product by the customer 30 or a further downstream customer 30. If the pellets 36 are off-spec, however, the customer 30 may return the pellets 36 to the polyolefin production facility 10 or may mix the pellets 36 with in-spec material to bring the aggregate within the specification.

To facilitate these decisions, the customer 30 may use a Raman device, such as the portable Raman device 100 discussed above, to check the properties of pellet samples prior to unloading the pellets 36 into the customer's storage site. Raman spectral data 202 may be obtained from a sample of the received pellets 36, such as density, comonomer content, modulus, crystallinity, melt flow rate, and/or melt index, determined at the site of receipt. Similarly, the customer 30 may determine the presence or distribution of one or more additives 586 on or in the pellets 36 from the spectral data 202. Based on the determined properties and/or additives, the customer 30 may accept the pellets 36, divert unsatisfactory pellets 36 to other operations, or return unsatisfactory pellets 36 to the supplier.

Similarly, the customer 30 or downstream customers 30 may use Raman spectrometry to acquire spectral data 202 of polyolefin products 620, whether final or intermediate, manufactured from the pellets 36, such as by former 622. Such spectral data 202 may be used to determine one or more properties of interest, whether physical, mechanical, rheological, and/or melt, prior to shipment or acceptance of the product 620. In this manner, a manufacturer may divert or terminate shipment of an unacceptable product 620 or a purchaser may refuse receipt of such a product 620.

While the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A method of operating a feed system for a polyolefin polymerization reactor, comprising the acts of:

exposing contents in a pumping mechanism within a feed system of a polyolefin polymerization reactor to a radiation emission from a spectroscopic probe;

acquiring a spectroscopic signal from the contents on-line in substantially real-time in response to the radiation emission via the spectroscopic probe; and analyzing the spectroscopic signal to determine a property of the contents.

2. The method as recited in claim 1, comprising the act of controlling the addition rate of the feed stream to the polymerization reactor in response to the property.

3. The method as recited in claim 1, comprising the act of mixing a plurality of feedstocks in the feed system.

4. The method as recited in claim 1, wherein the polymerization reactor comprises a loop slurry reactor adapted to polymerize an olefin to form a polyolefin.

5. The method as recited in claim 1, wherein the polyolefin comprises polyethylene, polyethylene copolymer, polypropylene, or polypropylene copolymer, or any combination thereof.

6. The method as recited in claim 1, wherein the property comprises a concentration in the contents of a monomer, a comonomer, a diluent, a catalyst, a co-catalyst, a donor agent, hydrogen, an inert component, a contaminant, or a catalyst poison, or any combination thereof.

7. The method as recited in claim 1, wherein the spectroscopic probe comprises a Raman probe.

8. A method of monitoring and controlling a polyolefin production process, comprising the acts of:
- receiving a feedstock into a feed system of a polymerization reactor;
- exposing contents in a pumping mechanism in the feed system to a radiation emission from a spectroscopic probe;
- acquiring a spectroscopic signal from the contents in substantially real-time in response to the radiation emission via the spectroscopic probe;
- analyzing the spectroscopic signal to determine a property of the contents; and
- adjusting an operation of the polyolefin production process based on the property.

9. The method as recited in claim 8, wherein the act of adjusting the operation of the polyolefin production process comprises the act of adjusting an addition rate of a feed stream to the polymerization reactor.

10. The method as recited in claim 9, wherein the act of adjusting the addition rate of the feed stream comprises the act of manipulating the operation of a flow controller, a valve, a compressor, or a pump, or any combination thereof.

11. The method as recited in claim 8, wherein the act of adjusting the operation of the polyolefin production process comprises the act of adjusting a concentration of a component in a feed stream to the polymerization reactor.

12. The method as recited in claim 11, wherein the act of adjusting the concentration of the component in the feed stream comprises the act of manipulating the operation of a flow controller, a valve, a compressor, or any pump, or any combination thereof.

13. The method as recited in claim 8, wherein the act of adjusting the operation of the polyolefin production process comprises the act of adjusting a concentration of a component in the polymerization reactor.

14. The method as recited in claim 13, wherein the component comprises a catalyst.

15. The method as recited in claim 14, wherein the concentration of the catalyst is adjusted to control a polyolefin polymer property in the polymerization reactor, a polyolefin solids concentration in the polymerization reactor, a production rate of a polyolefin in the polymerization reactor, or a polyolefin slurry density in the polymerization reactor, or any combination thereof.

16. The method as recited in claim 13, wherein the component comprises a comonomer.

17. The method as recited in claim 16, wherein the concentration of the comonomer is adjusted to control a polyolefin product density in the polymerization reactor.

18. The method as recited in claim 13, wherein the component comprises hydrogen.

19. The method as recited in claim 18, wherein the concentration of hydrogen is adjusted to control a polyolefin melt flow rate in the polymerization reactor, or a polyolefin melt index in the polymerization reactor, or any combination thereof.

20. The method as recited in claim 8, wherein the act of adjusting the operation of the polyolefin production process comprises the act of adjusting an operation of the feed system or the polymerization reactor, or a combination thereof, to facilitate a polyolefin grade transition in the polymerization reactor.

21. The method as recited in claim 8, wherein the spectroscopic probe comprises a Raman probe.

22. A method of using a Raman spectroscopic device in a polyolefin production process, comprising the acts of:
- exposing a feed for a polymerization reactor to a radiation emission from a Raman spectroscopic probe;
- acquiring a Raman spectroscopic signal from the feed in response to the radiation emission;
- analyzing the Raman spectroscopic signal to determine a property of the feed; and
- terminating an upstream supply of feedstock in response to the property.

23. The method as recited in claim 22, wherein the Raman spectroscopic signal is acquired via the Raman spectroscopic probe.

24. The method as recited in claim 22, wherein the feed comprises an olefin monomer, a comonomer, a diluent, a catalyst, a co-catalyst, a donor, or a chain transfer agent, or any combination thereof.

25. The method as recited in claim 24, wherein:
- the olefin monomer and the comonomer comprise ethylene, propylene, butene, hexene, octene, or decene, or a combination thereof;
- the diluent comprises isobutane, propane, n-pentane, i-pentane, neopentane, or n-hexane, or a combination thereof; and
- the chain transfer agent comprises hydrogen.

26. The method as recited in claim 22, wherein the feed comprises an on-line mixture in a feed system, the feed system configured to manage feed components and to deliver a feed stream to the polymerization reactor.

27. The method as recited in claim 22, wherein the Raman spectroscopic signal is acquired in substantially real-time.

28. The method as recited in claim 22, wherein the feed comprises an off-line sample collected from a feed system.

29. The method as recited in claim 22, wherein the property comprises a concentration of an olefin monomer, a comonomer, a diluent, a catalyst, a co-catalyst, a chain transfer agent, a donor, an inert component, a contaminant, and a catalyst poison, or any combination thereof.

30. A method of using a Raman spectroscopic device in a polyolefin production process, comprising the acts of:
- exposing a feed for a polymerization reactor to a radiation emission from a Raman spectroscopic probe;
- acquiring a Raman spectroscopic signal from the feed in response to the radiation emission;
- analyzing the Raman spectroscopic signal to determine a property of the feed; and
- notifying a supplier of a feedstock to adjust a supplier operation in response to the property.

31. The method as recited in claim 22, comprising the act of adjusting a flow rate of a feed stream to the polymerization reactor in response to the property.

32. The method as recited in claim 22, comprising the act of adjusting a component concentration in a feed stream to the polymerization reactor in response to the property.

33. The method as recited in claim 22, comprising the act of adjusting a ratio of a first component to a second component in a feed stream to the polymerization reactor in response to the property.

34. A method of monitoring a polyolefin production process, comprising:
- receiving a feedstock into a feed system of a polyolefin reactor, wherein the feed system is configured to deliver a feed stream comprising the feedstock to the polyolefin reactor, and the polyolefin reactor is configured to polymerize at least one olefin in the presence of a catalyst into a polyolefin;
- placing a Raman spectroscopic probe tip into a process volume in the feed system;

exposing contents in the process volume to a radiation emission from a Raman spectroscopic probe;

acquiring a Raman spectroscopic signal from the contents in substantially real-time in response to the radiation emission via the spectroscopic probe;

analyzing the Raman spectroscopic signal to determine a property of the contents; and notifying a supplier of the feedstock to adjust a supplier operation in response to the property.

35. The method as recited in claim 34, wherein the process volume comprises a conduit, a vessel, or a pumping mechanism, or a combination thereof.

36. The method as recited in claim 34, wherein the feed stream passes through the process volume.

37. The method as recited in claim 34, comprising the act of adjusting a feed rate to a polymerization reactor, a feed concentration to the polymerization reactor, or a concentration in the polymerization reactor, or any combination thereof, in response to the property.

38. A process for manufacturing a product comprising a polyolefin, the process comprising the act of:

manufacturing a product at least a portion of which comprises a polyolefin, wherein the polyolefin is produced by a method comprising the acts of:

receiving a feedstock into a feed system of a polymerization reactor, wherein the feed system is configured to deliver a feed stream comprising the feedstock to the polymerization reactor, and the polymerization reactor is configured to polymerize at least one olefin in the presence of a catalyst into the polyolefin;

exposing contents on-line in the feed system to a radiation emission from a spectroscopic probe;

acquiring a spectroscopic signal from the contents in substantially real-time in response to the radiation emission via the spectroscopic probe;

analyzing the spectroscopic signal to determine a property of the contents; and terminating an upstream supply of feedstock in response to the property.

39. The process as recited in claim 38, wherein the spectroscopic probe comprises a Raman probe.

40. The process as recited in claim 38, comprising the act of obtaining the polyolefin.

41. The process as recited in claim 38, wherein the act of manufacturing comprises the act of processing the polyolefin to form the product or to form a polyolefin component of the product, or any combination thereof.

42. The process as recited in claim 41, wherein the act of processing comprises the act of blending, heating, melting, extruding, injection-molding, blow-molding, forming a film, incorporating an additive, or any combination thereof.

43. The process as recited in claim 38, wherein the act of manufacturing comprises the act of assembling a component formed from the polyolefin into the product.

44. The process as recited in claim 38, comprising the act of shipping the product or shipping a polyolefin component of the product, or a combination thereof.

45. The process as recited in claim 38, wherein the polyolefin comprises high density polyethylene (HDPE), low density polyethylene (LDPE), linear low density polyethylene (LLDPE), isotactic polypropylene (iPP), or syndiotactic polypropylene (sPP), or a combination thereof.

46. The process as recited in claim 38, wherein the product comprises film, piping, food packaging, beverage packaging, retail packaging, pharmaceutical packaging, furniture, carpeting, a consumer electronic, a household container, a household appliance, a toy, an automobile component, or an agricultural product, or a combination thereof.

* * * * *